United States Patent
Patil et al.

(10) Patent No.: US 9,422,499 B2
(45) Date of Patent: *Aug. 23, 2016

(54) LOW VISCOSITY, LOW VOLATILITY LUBRICATING OIL BASESTOCKS

(71) Applicant: ExxonMobil Research and Engineering Company, Annandale, NJ (US)

(72) Inventors: Abhimanyu O. Patil, Westfield, NJ (US); Satish Bodige, Wayne, NJ (US); Mark P. Hagemeister, Houston, TX (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/630,022

(22) Filed: Feb. 24, 2015

(65) Prior Publication Data

US 2015/0275117 A1   Oct. 1, 2015

Related U.S. Application Data

(60) Provisional application No. 61/972,512, filed on Mar. 31, 2014.

(51) Int. Cl.
| | | |
|---|---|---|
| *C07F 7/08* | (2006.01) |
| *C07C 69/34* | (2006.01) |
| *C08K 5/01* | (2006.01) |
| *C10M 135/22* | (2006.01) |
| *C07F 7/04* | (2006.01) |
| *C07C 319/00* | (2006.01) |
| *C10M 105/76* | (2006.01) |
| *C10M 105/72* | (2006.01) |
| *C07C 321/20* | (2006.01) |
| *C07F 7/18* | (2006.01) |
| *C10M 135/04* | (2006.01) |
| *C10M 135/24* | (2006.01) |
| *C10M 135/26* | (2006.01) |
| *C10M 135/28* | (2006.01) |
| *C10M 135/30* | (2006.01) |
| *C10M 139/04* | (2006.01) |
| *C10M 159/12* | (2006.01) |
| *C10M 177/00* | (2006.01) |

(52) U.S. Cl.
CPC ............ *C10M 105/76* (2013.01); *C07C 321/20* (2013.01); *C07F 7/1804* (2013.01); *C10M 105/72* (2013.01); *C10M 135/04* (2013.01); *C10M 135/22* (2013.01); *C10M 135/24* (2013.01); *C10M 135/26* (2013.01); *C10M 135/28* (2013.01); *C10M 135/30* (2013.01); *C10M 139/04* (2013.01); *C10M 159/12* (2013.01); *C10M 177/00* (2013.01); *C10M 2219/02* (2013.01); *C10M 2219/021* (2013.01); *C10M 2219/022* (2013.01); *C10M 2227/04* (2013.01); *C10M 2227/045* (2013.01); *C10N 2220/021* (2013.01); *C10N 2220/022* (2013.01); *C10N 2230/02* (2013.01); *C10N 2230/04* (2013.01); *C10N 2230/70* (2013.01); *C10N 2230/74* (2013.01); *C10N 2270/00* (2013.01)

(58) Field of Classification Search
CPC ............ C10M 2227/04; C07F 7/1892; C07C 319/00
USPC ........ 508/207, 305, 516, 569, 465; 556/427; 568/58

See application file for complete search history.

(56) References Cited

U.S. PATENT DOCUMENTS

| | | |
|---|---|---|
| 3,036,003 A | 5/1962 | Verdol |
| 3,172,892 A | 3/1965 | Le Suer et al. |
| 3,219,666 A | 11/1965 | Norman et al. |
| 3,316,177 A | 4/1967 | Dorer, Jr. |
| 4,076,639 A * | 2/1978 | Bridger .................. C07C 323/00 252/77 |

(Continued)

FOREIGN PATENT DOCUMENTS

| | | |
|---|---|---|
| EP | 410849 A1 | 1/1991 |
| EP | 834543 A1 | 4/1998 |

(Continued)

OTHER PUBLICATIONS

The International Search Report and Written Opinion of PCT/US2015/017630 dated Oct. 1, 2015.
Nagamoto, Yuuki et al., "Synthesis of Functionalized Polycyclic Aromatic Compounds via a Formal [2+2]-Cycloaddition," Organic Letters, 2014, vol. 16, No. 3, pp. 1008-1011.
Wei, Yanhu et al., "Scanning Tunneling Microscopy of Prochiral Anthracene Derivatives on Graphite: Chain Length Effects on Monolayer Morphology," Journal of the American Chemical Society, 2004, vol. 126, No. 16, pp. 5318-5322.

*Primary Examiner* — Vishal Vasisth
(74) *Attorney, Agent, or Firm* — Robert A. Migliorini

(57) ABSTRACT

A composition containing one or more sulfur-containing compounds represented by the formula $(R_1)_a(X)(R_2)_b$ wherein $R_1$ and $R_2$ are the same or different and are the residue of an olefin (e.g., aliphatic, aromatic or cycloaliphatic olefin) having from 4 to 40 carbon atoms, X is the residue of a thiol or polythiol, $\underline{a}$ is a value from 1 to 6, and $\underline{b}$ is a value from 0 to 6. The composition has a kinematic viscosity at 100° C. ($Kv_{100}$) from 2 to 300 cst, a kinematic viscosity at 40° C. ($Kv_{40}$) from 5 to 4000 cst, a viscosity index (VI) from −100 to 300, and a Noack volatility of no greater than 90 percent. A process for producing the composition, a lubricating oil base stock and lubricating oil containing the composition, and a method for improving one or more of solubility and dispersancy of polar additives in a lubricating oil containing the composition.

22 Claims, No Drawings

(56) References Cited

U.S. PATENT DOCUMENTS

| | | | |
|---|---|---|---|
| 4,135,047 A * | 1/1979 | Morgan | C08G 75/045 544/219 |
| 4,234,435 A | 11/1980 | Meinhardt et al. | |
| 4,827,064 A | 5/1989 | Wu | |
| 4,827,073 A | 5/1989 | Wu | |
| 4,889,647 A | 12/1989 | Rowan et al. | |
| 4,956,122 A | 9/1990 | Watts et al. | |
| 4,978,464 A | 12/1990 | Coyle et al. | |
| 5,705,458 A | 1/1998 | Roby et al. | |
| 2013/0109604 A1 | 5/2013 | Patil et al. | |
| 2014/0121143 A1 | 5/2014 | Patil et al. | |

FOREIGN PATENT DOCUMENTS

| | | |
|---|---|---|
| EP | 1040115 B1 | 6/2004 |
| WO | 99/31113 A1 | 6/1999 |
| WO | 2007/011973 A1 | 1/2007 |

\* cited by examiner

LOW VISCOSITY, LOW VOLATILITY LUBRICATING OIL BASESTOCKS

CROSS-REFERENCE TO RELATED APPLICATIONS

This application claims priority to U.S. Provisional Application Ser. No. 61/972,512 filed Mar. 31, 2014, which is herein incorporated by reference in its entirety.

RELATED APPLICATIONS

This application is related to U.S. patent application Ser. No. 13/660,122 filed on Oct. 25, 2012 and U.S. patent application Ser. No. 13/660,152 filed on Oct. 25, 2012. This application is also related to two other co-pending applications, filed on even date herewith, and identified by the following U.S. Ser. No. 14/630,036 entitled "Low Viscosity, Low Volatility Lubricating Oil Basestocks" and U.S. Ser. No. 14/630,065 entitled "Low Viscosity, Low Volatility Lubricating Oil Basestocks"; all of which are incorporated herein in their entirety by reference.

FIELD

This disclosure relates to low viscosity, low volatility compositions that include one or more sulfur-containing compounds, a process for producing the compositions, a lubricating oil base stock and lubricating oil containing the composition, and a method for improving one or more of solubility and dispersancy of polar additives in a lubricating oil by using as the lubricating oil a formulated oil containing the composition.

BACKGROUND

Lubricants in commercial use today are prepared from a variety of natural and synthetic base stocks admixed with various additive packages and solvents depending upon their intended application. The base stocks typically include mineral oils, polyalphaolefins (PAO), gas-to-liquid base oils (GTL), silicone oils, phosphate esters, diesters, polyol esters, and the like.

A major trend for passenger car engine oils (PCEOs) is an overall improvement in quality as higher quality base stocks become more readily available. Typically the highest quality PCEO products are formulated with base stocks such as PAOs or GTL stocks.

PAOs and GTL stocks are an important class of lube base stocks with many excellent lubricating properties, including high viscosity index (VI) but have low polarity. This low polarity leads to low solubility and dispersancy for polar additives and/or sludge generated during service. These base stocks require the use of cobase stocks to improve additive and deposit solubility.

Therefore, there is a need for polar cobase fluids that provide appropriate solubility and dispersibility for polar additives and/or sludge generated during service of lubricating oils.

The present disclosure also provides many additional advantages, which shall become apparent as described below.

SUMMARY

This disclosure relates in part to a composition comprising one or more sulfur-containing compounds represented by the formula

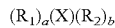

$(R_1)_a(X)(R_2)_b$ wherein $R_1$ and $R_2$ are the same or different and are the residue of an olefin having from about 4 to about 40 carbon atoms, X is the residue of a thiol or polythiol, $\underline{a}$ is a value from 1 to about 6, and $\underline{b}$ is a value from 0 to about 6. The olefin is selected from the group consisting of an aliphatic olefin, an aromatic olefin, and a cycloaliphatic olefin. The thiol is selected from the group consisting of an aliphatic thiol, an aromatic thiol, a cycloaliphatic thiol, an ether-, ester- or acid-containing thiol, and a heteroatom-containing thiol. The polythiol is selected from the group consisting of an aliphatic polythiol, an aromatic polythiol, a cycloaliphatic polythiol, an ether-, ester- or acid-containing polythiol, and a heteroatom-containing polythiol. The composition has a kinematic viscosity at a temperature of 100° C. ($Kv_{100}$), measured according to ASTM standard D-445, from about 2 to about 300 cst, a kinematic viscosity at a temperature of 40° C. ($Kv_{40}$), measured according to ASTM standard D-445, from about 5 to about 4000 cst, a viscosity index (VI), measured according to ASTM standard D-2270, from about −100 to about 300, and a Noack volatility, measured according to ASTM D-5800, of no greater than about 90 percent.

This disclosure also relates in part to a composition comprising one or more sulfur-containing compounds. The one or more sulfur-containing compounds are produced by a process which comprises reacting an olefin with a thiol or polythiol, optionally in the presence of a catalyst, under thiol-ene reaction conditions sufficient to produce the one or more sulfur-containing compounds. The olefin is selected from the group consisting of an aliphatic olefin, an aromatic olefin, and a cycloaliphatic olefin. The thiol is selected from the group consisting of an aliphatic thiol, an aromatic thiol, a cycloaliphatic thiol, an ether-, ester- or acid-containing thiol, and a heteroatom-containing thiol. The polythiol is selected from the group consisting of an aliphatic polythiol, aromatic polythiol, cycloaliphatic polythiol, an ether-, ester- or acid-containing polythiol, and a heteroatom-containing polythiol. The composition has a kinematic viscosity at a temperature of 100° C. ($Kv_{100}$), measured according to ASTM standard D-445, from about 2 to about 300 cst, a kinematic viscosity at a temperature of 40° C. ($Kv_{40}$), measured according to ASTM standard D-445, from about 5 to about 4000 cst, a viscosity index (VI), measured according to ASTM standard D-2270, from about −100 to about 300, and a Noack volatility, measured according to ASTM D-5800, of no greater than about 90 percent.

This disclosure further relates in part to a process for producing a composition comprising one or more sulfur-containing compounds. The process comprises reacting an olefin with a thiol or polythiol, optionally in the presence of a catalyst, under thiol-ene reaction conditions sufficient to produce the composition. The olefin is selected from the group consisting of an aliphatic olefin, an aromatic olefin, and a cycloaliphatic olefin. The thiol is selected from the group consisting of an aliphatic thiol, an aromatic thiol, a cycloaliphatic thiol, an ether-, ester- or acid-containing thiol, and a heteroatom-containing thiol. The polythiol is selected from the group consisting of an aliphatic polythiol, aromatic polythiol, cycloaliphatic polythiol, an ether-, ester- or acid-containing polythiol, and a heteroatom-containing polythiol. The composition has a kinematic viscosity at a temperature of 100° C. ($Kv_{100}$), measured according to ASTM standard D-445, from about 2 to about 300 cst, a kinematic viscosity at a temperature of 40° C. ($Kv_{40}$), measured according to ASTM standard D-445, from about 5 to about 4000 cst, a viscosity index (VI), measured according to ASTM standard D-2270, from about −100 to about 300, and a Noack volatility, measured according to ASTM D-5800, of no greater than about 90 percent.

This disclosure yet further relates in part to a lubricating oil base stock comprising one or more compounds represented by the formula

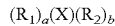

wherein $R_1$ and $R_2$ are the same or different and are the residue of an olefin having from about 4 to about 40 carbon atoms, X is the residue of a thiol or polythiol, $\underline{a}$ is a value from 1 to about 6, and $\underline{b}$ is a value from 0 to about 6. The olefin is selected from the group consisting of an aliphatic olefin, an aromatic olefin, and a cycloaliphatic olefin. The thiol is selected from the group consisting of an aliphatic thiol, an aromatic thiol, a cycloaliphatic thiol, an ether-, ester- or acid-containing thiol, and a heteroatom-containing thiol. The polythiol is selected from the group consisting of an aliphatic polythiol, aromatic polythiol, cycloaliphatic polythiol, an ether-, ester- or acid-containing polythiol, and a heteroatom-containing polythiol. The lubricating oil base stock has a kinematic viscosity at a temperature of 100° C. ($Kv_{100}$), measured according to ASTM standard D-445, from about 2 to about 300 cst, a kinematic viscosity at a temperature of 40° C. ($Kv_{40}$), measured according to ASTM standard D-445, from about 5 to about 4000 cst, a viscosity index (VI), measured according to ASTM standard D-2270, from about −100 to about 300, and a Noack volatility, measured according to ASTM D-5800, of no greater than about 90 percent.

This disclosure also relates in part to a lubricating oil comprising a lubricating oil base stock as a major component, and a sulfur-containing cobase stock as a minor component. The sulfur-containing cobase stock comprises one or more compounds represented by the formula

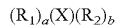

wherein $R_1$ and $R_2$ are the same or different and are the residue of an olefin having from about 4 to about 40 carbon atoms, X is the residue of a thiol or polythiol, $\underline{a}$ is a value from 1 to about 6, and $\underline{b}$ is a value from 0 to about 6. The olefin is selected from the group consisting of an aliphatic olefin, an aromatic olefin, and a cycloaliphatic olefin. The thiol is selected from the group consisting of an aliphatic thiol, an aromatic thiol, a cycloaliphatic thiol, an ether-, ester- or acid-containing thiol, and a heteroatom-containing thiol. The polythiol is selected from the group consisting of an aliphatic polythiol, aromatic polythiol, cycloaliphatic polythiol, an ether-, ester- or acid-containing polythiol, and a heteroatom-containing polythiol. The sulfur-containing cobase stock has a kinematic viscosity at a temperature of 100° C. ($Kv_{100}$), measured according to ASTM standard D-445, from about 2 to about 300 cst, a kinematic viscosity at a temperature of 40° C. ($Kv_{40}$), measured according to ASTM standard D-445, from about 5 to about 4000 cst, a viscosity index (VI), measured according to ASTM standard D-2270, from about −100 to about 300, and a Noack volatility, measured according to ASTM D-5800, of no greater than about 90 percent.

This disclosure further relates in part to a method for improving one or more of solubility and dispersancy of polar additives in a lubricating oil by using as the lubricating oil a formulated oil comprising a lubricating oil base stock as a major component, and a sulfur-containing cobase stock as a minor component. The sulfur-containing cobase stock comprises one or more compounds represented by the formula

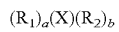

wherein $R_1$ and $R_2$ are the same or different and are the residue of an olefin having from about 4 to about 40 carbon atoms, X is the residue of a thiol or polythiol, $\underline{a}$ is a value from 1 to about 6, and $\underline{b}$ is a value from 0 to about 6. The olefin is selected from the group consisting of an aliphatic olefin, an aromatic olefin, and a cycloaliphatic olefin. The thiol is selected from the group consisting of an aliphatic thiol, an aromatic thiol, a cycloaliphatic thiol, an ether-, ester- or acid-containing thiol, and a heteroatom-containing thiol. The polythiol is selected from the group consisting of an aliphatic polythiol, aromatic polythiol, cycloaliphatic polythiol, an ether-, ester- or acid-containing polythiol, and a heteroatom-containing polythiol. The sulfur-containing cobase stock has a kinematic viscosity at a temperature of 100° C. ($Kv_{100}$), measured according to ASTM standard D-445, from about 2 to about 300 cst, a kinematic viscosity at a temperature of 40° C. ($Kv_{40}$), measured according to ASTM standard D-445, from about 5 to about 4000 cst, a viscosity index (VI), measured according to ASTM standard D-2270, from about −100 to about 300, and a Noack volatility, measured according to ASTM D-5800, of no greater than about 90 percent.

This disclosure provides sulfur-containing polar and hydrolytically stable Group V basestocks. The sulfur-containing fluids of this disclosure have surprisingly good lubricant properties. Moreover, the sulfur-containing fluids of this disclosure have surprisingly improved viscosity and volatility characteristics in comparison with PAOs.

Further, in addition to improved solubility and dispersibility for polar additives and/or sludge generated during service of lubricating oils, improved fuel efficiency can also be attained in an engine lubricated with a lubricating oil by using as the lubricating oil a formulated oil in accordance with this disclosure. The formulated oil comprises a lubricating oil base stock as a major component, and a sulfur-containing cobase stock as a minor component. The lubricating oils of this disclosure are particularly advantageous as passenger vehicle engine oil (PVEO) products. Optionally, the formulated oil comprises a lubricating oil basestock as a minor component, and a sulfur-containing, lubricating oil cobasestock as a major component.

Further objects, features and advantages of the present disclosure will be understood by reference to the following drawings and detailed description.

DETAILED DESCRIPTION

All numerical values within the detailed description and the claims herein are modified by "about" or "approximately" the indicated value, and take into account experimental error and variations that would be expected by a person having ordinary skill in the art.

In an embodiment, this disclosure relates to low viscosity, low volatility (LVLV) sulfur-containing synthetic base stocks. An olefin such as an aliphatic olefin, an aromatic olefin, or a cycloaliphatic olefin, is reacted with a thiol such as an aliphatic thiol, an aromatic thiol, a cycloaliphatic thiol, an ether-, ester- or acid-containing thiol, or a heteroatom-containing thiol, or a polythiol such as an aliphatic polythiol, aromatic polythiol, cycloaliphatic polythiol, an ether-, ester- or acid-containing polythiol, or a heteroatom-containing polythiol, to obtain synthetic base stocks. The products exhibit good lubricant properties.

The compositions of this disclosure possess low viscosity, low Noack volatility and superior low temperature properties. The compositions of this disclosure exhibit excellent bulk flow properties with built-in polarity.

As indicated above, the compositions of this disclosure comprise one or more sulfur-containing compounds represented by the formula

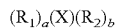

wherein $R_1$ and $R_2$ are the same or different and are the residue of an olefin having from about 4 to about 40 carbon atoms, X is the residue of a thiol or polythiol, <u>a</u> is a value from 1 to about 6, and <u>b</u> is a value from 0 to about 6. The olefin is selected from the group consisting of an aliphatic olefin, an aromatic olefin, and a cycloaliphatic olefin. The thiol is selected from the group consisting of an aliphatic thiol, an aromatic thiol, a cycloaliphatic thiol, an ether-, ester- or acid-containing thiol, and a heteroatom-containing thiol. The polythiol is selected from the group consisting of an aliphatic polythiol, an aromatic polythiol, a cycloaliphatic polythiol, an ether-, ester- or acid-containing polythiol, and a heteroatom-containing polythiol.

Illustrative $R_1$ and $R_2$ substituents include, for example, the residue of aliphatic olefins, aromatic olefins and cycloaliphatic olefins.

Illustrative aliphatic olefins include, for example, $C_4$-$C_{40}$ alkane hydrocarbons, the residue of polyalphaolefin (e.g., mPAO) dimers ($C_6$-$C_{40}$), trimers ($C_6$-$C_{40}$), tetramers ($C_6$-$C_{40}$) and higher oligomers, pentamer, hexamer, and the like, or alpha-olefin ($C_4$-$C_{40}$). Suitable alpha-olefins include, for example, alkyl olefins such as 1-decene, 1-octene, 1-dodecene, 1-hexene, 1-tetradecene, 1-octadecene, and the like.

The mPAO dimer can be any dimer prepared from metallocene or other single-site catalyst with terminal double bond. The dimer can be from 1-decene, 1-octene, 1-dodecene, 1-hexene, 1-tetradecene, 1-octadecene or combination of alpha-olefins. A metallocene-catalyzed alpha-olefin oligomerization process is described in WO 2007/011973, which is incorporated herein by reference in its entirety and to which reference is made for details of feeds, metallocene catalysts, process conditions and characterizations of products.

Illustrative aromatic olefins include, for example, 2,4-dimethylstyrene, 2,5-dimethylstyrene, 4-tert-butylstyrene, 4-tert-butoxystyrene, 3,4-dimethoxystyrene, 4-acetoxystyrene, 1,3-diisopropenylbenzene, 4-ethoxystyrene, 2,3,4,5,6-pentafluorostyrene, 4-fluorostyrene, 1-(trifluoromethyl)-4-vinylbenzene, 4-[N-(methylaminoethyl)aminomethyl]styrene, 4-benzyloxy-3-methoxystyrene, 2-methoxy-4-vinylphenol, ((4-vinylphenyl)methylene)dibenzene, 1-vinylnaphthalene, 2-vinylnaphthalene, divinylbenzene, trivinylbenzene, styrene, 4-methyl styrene, 2-methyl styrene, 1-methyl styrene, 4-methoxystyrene, 2-methoxystyrene, 1-allyl-4-(trifluoromethyl)benzene, 9-vinylanthracene, 1,1-diphenylethylene, 2,3-dibenzyl-1,3-butadiene, 1-allyl-2-methylbenzene, dipentene, 4-vinylbiphenyl, 9-vinylcarbazole, N-vinylphthalimide, 4-(trifluoromethyl)styrene, and the like.

Illustrative cycloaliphatic olefins include, for example, vinylcyclopentane, vinylcylcohexane, allylcyclohexane, 1,2,4-trivinylcyclohexane, 5-vinyl-2-norbornene, and the like.

Illustrative X substituents include, for example, the residue of thiols and polythiols. Illustrative thiols include, for example, an aliphatic thiol, an aromatic thiol, a cycloaliphatic thiol, an ether-, ester- or acid-containing thiol, a heteroatom-containing thiol, and the like. Illustrative polythiols include, for example, an aliphatic polythiol, an aromatic polythiol, a cycloaliphatic polythiol, an ether-, ester- or acid-containing polythiol, a heteroatom-containing polythiol, and the like.

Illustrative thiols useful in this disclosure include, for example, $C_4$-$C_{20}$ alkyl thiols, 1-butanethiol, 1-hexanethiol, 2-ethylhexylthiol, 1-dodecanethiol, benzyl thiol, cyclopentyl thiol, cyclohexyl thiol, and the like. The thiols can be primary or secondary, linear or branched thiols with alkyl carbon chain length of $C_4$-$C_{20}$ carbons. Higher thiols in the range $C_6$-$C_{18}$ are of particular industrial significance. This disclosure encompasses the whole group of primary and secondary, branched and unbranched, even- and odd-numbered thiols.

Illustrative aliphatic thiols include, for example, 1-butanethiol, 1-hexanethiol, 1-octanethiol, 1-decanehiol, 1-dodecanethiol, 1-hexadecanethiol, 1-octadecanethiol, and the like.

Other illustrative aliphatic thiols useful in this disclosure include, for example, methanethiol (m-mercaptan), ethanethiol (e-mercaptan), 1-propanethiol (n-P mercaptan), 2-propanethiol (2C3 mercaptan), 1-butanethiol, (n-butyl mercaptan), tert-butyl mercaptan, 1-pentane thiols (pentyl mercaptan), 1-hexanethiol, 1-heptane thiols (heptyl mercaptan), 1-octanethiol, 1-nonanethiol, 1-decanethiol, 1-dodecanethiol, 1-hexadecanethiol, 1-octadecanethiol, cyclohexanethiol, 2,4,4-trimethyl-2-pentanethiol, and the like, or combination of those. One can also use functional thio-alkanes to react with mPAO dimer. Examples of functional thio-alkane include mercaptoethyoxy ethanol (HO—$CH_2$—$CH_2$—O—$CH_2$—$CH_2$—SH), ethanethio, 2-ethoxy-($CH_3$—$CH_2$—O—$CH_2$—$CH_2$—SH), 1-mercapto-4,7,10-trioxaundecane (HS—$CH_2$—$CH_2$—O—$CH_2$—$CH_2$—O—$CH_2$—$CH_2$—O—$CH_3$), 2-(2-methoxyethoxyl)ethanethiol, 2-(trimethylsilyl)ethanethiol, 2,2,2-trifluoroethanethiol, 5-mercapto-4H-[1,2,4]triazol-3-ol, thioglycolic acid, 2-mercaptoethanol, cysteamine, thiolactic acid, methylthioglycolate, 2-methoxyethanethiol, 2-mercaptoethyl ether, methylthioglycolate, 2-propene-1-thiol, 3-chloro-1-propanethiol, L-cysteine, 1-mercapto-2-propanol, 3-mercapto-1-propanol, 4-mercaptobutyric acid, 2-butanethiol, 2-(2-methoxyethoxyl)ethanethiol, 3-mercapto-3-methyl-1-butyl-1-formate, 3-mercaptobutylacetate, 3-mercapto-1-hexanol, 6-mercapto-1-hexanol, 2-(butylamino)ethanethiol, 2-ethylhexyl thioglycolate, 3-mercaptohexyl butyrate, 3-mercaptopropionic acid, 8-mercaptooctanoic acid, 8-mercapto-1-octanol, 11-mercaptoundecanoic acid, 12-mercaptoundecanoic acid, 16-mercaptoundecanoic acid, trimethylopropane tris (3-mercaptopropionate), 3-mercaptohexylhexaanote, 2-ethylhexanethiol, O-[2-(3-mercaptopropionylamino)ethyl]-O'-methylpolyethylene glycol, O-(2-carboxyethyl)-O'-(2-mercaptoethyl)heptaethylene glycol, O-(2-mercaptoethyl)-O'-methyl-hexa(ethylene glycol), Mn=350, poly(ethylene glycol) methyl ether thiol, Mn=1000, poly(ethylene glycol) 2-mercaptoethylether acetic acid, Mn=1500.

Illustrative aromatic thiols include, for example, thiophenol, 4-methylbenzenethiol, 4-methoxythiophenol, benzyl mercapton, 4-mercaptopyridine, 2-mercaptopyrimidine, 1-naphthalenethiol, 2-naphthalenethiol, and the like.

Other illustrative aromatic thiols useful in this disclosure include, for example, benzenethiol, thiophenol, 2,3,4,5,6,-pentafluorothiophenol, 2,3,5,6-tetrafluorophenol, 2,3-dichlorothiophenol, 2,4-dichlorothiophenol, 2,5-dichlorothiophenol, 3,4-dichlorothiophenol, 3,5-dichlorothiophenol, 2,4-diflurothiophenol, 3,4-diflurothiophenol, 2-bromothiophenol, 3-bromothiophenol, 4-bromothiophenol, 2-chlorothiophenol, 3-chlorothiophenol, 4-chlorothiophenol, 2-fluorothiophenol, 3-fluorothiophenol, 4-fluorothiophenol, 2-chlorobenzenemethanethiol, 4-chlorobenzenemethanethiol, (3-nitrobenzyl) marcaptan, (4-nitrobenzyl)marcaptan, 2-mercaptobenzeyl alcohol, 4-nitrothiophenol, 2-mercaptophenol, 3-mercaptophenol, 4-mercaptophenol, 2-aminothiophenol, 3-aminothiophenol, 4-aminothiophenol, 2-(trifluoromethyl)benzenethiol, 4-bromo-2-fluorobenzyl mercaptan, 4-chloro-2-fluorobenzyl mercaptan, 3,4-difluorobenzyl mercaptan, 3,5-difluorobenzyl mercaptan, 2-bromobenzyl mercaptan, 3-bromobenzyl mercaptan, 4-bromobenzyl mercaptan, 3-fluorobenzyl mercaptan, 4-fluorobenzyl mercaptan, 2-methoxythiophenol, 3-methoxythiophenol, 4-methoxythiophenol, 2-methylbenzenethiol, 3-methylbenzenethiol, benzylmercaptan, 4-(methylsulfanyl)thiophenol, 2-phenoxyethanethiol, 3-ethoxythiolphenol, 4-methoxy-α-toluenethiol, 2,5-dimethoxythiphenol, 3,4-dimethoxythiphenol, 2,4-dimethylthiphenol, 2,5-dimethylthiphenol, 2,6-dimethylthiphenol, 1,3,5-dimethylthiphenol, 2,6-dimethylthiphenol, 2-ethylbenzenethiol, 2-phenylethanethiol, 1,2-benzenedimethanethiol, 1,3-benzenedimethanethiol, 1,4-benzenedimethanethiol, 2-isopropylbenzenethiol, 4-isopropylbenzenethiol, 4-(dimethylamino)thiophenol, 1-naphthalenethiol, 2-naphthalenethiol, 2,4,6-trimethylbenzyl mercaptan, 4-tert-butylbenzyl mercaptan, 4-tert-butylbenzenethiol, tert-dodecylmercaptan, triphenylmethanethiol, 9-fluorenylmethylthiol, 9-mercaptofluorene, and the like, or combination of those.

Illustrative cycloaliphatic thiols include, for example, cyclohexanethiol, cyclopentanethiol, 2-methylcyclopentanethiol, cyclodecanethiol, cyclododecanethiol, 3-decylcyclopentanethiol, (mercaptomethyl)cyclohexane, 3-isopropylcycloheptanethiol, 4-(2-mercaptoethyl)cyclohexanethiol, and the like.

Other illustrative cycloaliphatic thiols useful in this disclosure include, for example, cyclohexylthiol, cyclopenanethiol, 1-adamantanethiol, and the like, or combination of those.

Illustrative ether-, ester- or acid-containing thiols include, for example, butyl 3-mercaptopropionic acid, isooctyl 3-mercaptopropionate, methyl 3-mercaptopropionate, 3-mercaptopropionic acid, 2-ethylhexyl 2-mercaptoacetate, ethyl 2-mercaptopropionic acid, thioglycolic acid, and the like.

Other illustrative ester or acid containing thiols useful in this disclosure include, for example, 3-mercaptopropionate, 3-mercaptobenzoic acid, 4-mercaptobenzoic acid, thiosalicylic acid, and the like, or combination of those. Illustrative ester or acid containing polythiols (e.g., dithiols) useful in the process of this disclosure include, for example, pentaerythritoltetrakis(3-mercaptopropionate), trimethylopropanetris(3-mercaptopropionate), trimethylopropanetris(2-mercaptoacetate), and the like, or a combination of those.

Illustrative heteroatom-containing thiols include, for example, 3-mercaptopropyl)methyldimethoxysilane, 3-mercaptopropyl)trimethoxysilane, 3-mercaptopropyl) triethoxysilane, and the like.

Illustrative polythiols useful in this disclosure include, for example, 1,2-ethanedithiol, 3-mercaptopropionate, pentaerythritoltetrakis(3-mercaptopropionate), trimethylopropanetris(3-mercaptopropionate), and the like. The polythiols can be primary or secondary, linear or branched thiols with alkyl carbon chain length of $C_6$-$C_{20}$ carbons. Higher polythiols in the range $C_6$-$C_{18}$ are of particular industrial significance. This disclosure encompasses the whole group of primary and secondary, branched and unbranched, even- and odd-numbered polythiols.

Illustrative aliphatic polythiols include, for example, 1,2-ethanedithiol, 1,3-propanedithiol, 1,4-butanedithiol, 1,5-pentanedithiol, 1,6-hexanedithiol, 1,8-octanedithiol, 1,9-nonanedithiol, 1,11-undecanedithiol, 1,16-hexadecanedithiol, and the like.

Other illustrative aliphatic polythiols (e.g., dithiols) useful in this disclosure include, for example, 1,2-ethanedithiol, 1,11-undecanedithiol, 1,16-hexadecanedithiol, 1,3-propanedithiol, 1,4-butanedithiol, 1,5-pentanedithiol, 1,6-hexanethiol, 1,8-octanedithiol, 1,9-nonanedithiol, hexa(ethylene glycol)dithiol, tetra(ethylene glycol)dithiol, cyclohexanethiol, 2,4,4-trimethyl-2-pentanethiol, and the like, or a combination of those. One can also use functional thio-alkanes to react with mPAO dimer. Examples of functional thio-alkane include mercaptoethyoxy ethanol (HO—$CH_2$—$CH_2$—O—$CH_2$—$CH_2$—SH), ethanethio, 2-ethoxy-($CH_3$—$CH_2$—O—$CH_2$—$CH_2$—SH), 1-mercapto-4,7,10-trioxaundecane (HS—$CH_2$—$CH_2$—O—$CH_2$—$CH_2$—O—$CH_2$—$CH_2$—O—$CH_3$), 2-(2-methoxyethoxyl)ethanethiol, 2-(trimethylsilyl)ethanethiol, 2,2,2-trifluoroethanethiol, 5-mercapto-4H-[1,2,4]triazol-3-ol, thioglycolic acid, 2-mercaptoethanol, cysteamine, thiolactic acid, methylthioglycolate, 2-methoxyethanethiol, 2-mercaptoethyl ether, methylthioglycolate, 2-propene-1-thiol, 3-chloro-1-propanethiol, L-cysteine, 1-mercapto-2-propanol, 3-mercapto-1-propanol, 4-mercaptobutyric acid, 2-butanethiol, 2-(2-methoxyethoxyl)ethanethiol, 3-mercapto-3-methyl-1-butyl-1-formate, 3-mercaptobutylacetate, 3-mercapto-1-hexanol, 6-mercapto-1-hexanol, 2-(butylamino)ethanethiol, 2-ethylhexyl thioglycolate, 3-mercaptohexyl butyrate, 3-mercaptopropionic acid, 8-mercaptooctanoic acid, 8-mercapto-1-octanol, 11-mercaptoundecanoic acid, 12-mercaptoundecanoic acid, 16-mercaptoundecanoic acid, trimethylpropane tris (3-mercaptopropionate), 3-mercaptohexylhexaanote, 2-ethylhexanethiol, O-[2-(3-mercaptopropionylamino)ethyl]-O'-methylpolyethylene glycol, O-(2-carboxyethyl)-O'-(2-mercaptoethyl)heptaethylene glycol, O-(2-mercaptoethyl)-O'-methyl-hexa(ethylene glycol), Mn=350, poly(ethylene glycol) methyl ether thiol, Mn=1000, poly(ethylene glycol) 2-mercaptoethylether acetic acid, Mn=1500.

Illustrative aromatic polythiols include, for example, benzene-1,2-dithiol, benzene-1,3-dithiol, toluene-3,4-dithiol, 5-phenyl-1,3,4-oxadiazole-2-thiol, 1,3,4-thiodizole-2,5-dithiol, 1,2,4-thiadiazole-3,5-dithiol, and the like.

Other illustrative aromatic polythiols (e.g., dithiols) useful in this disclosure include, for example, benzene-1,2-dithiol, benzene-1,3-dithiol, toluene-3,4-dithiol, biphenyl-4,4'-dithiol, 1,3-propanethiol, 2,3-dimercapto-1-propanol, 1,4-butanedithiol, 2,2'-thiodiethanethiol, 1,2-ethanedithiol, 1,4-butanedithiol, 1,5-pentanedithiol, 1,6-hexanedithiol, 1,11-undecanedithiol, 1,16-hexadecanedithiol, 1,9-nonanedithiol, 1,4-dithioerythritol, 2,2'-thiodiethanethiol, 2,3-butanedithiol, hexa(ethylene glycol) dithiol, tetra(ethylene glycol) dithiol, 2,2'-[ethylenedioxy]diethanethiol, 2-mercaptoethylether, poly(ethylene glycol)dithiol, 1,2-benzenedimethanedithiol, 1,3-benzenedimethanedithiol, 1,4-benzenedimethanedithiol, and the like, or a combination of those.

Illustrative cycloaliphatic polythiols include, for example, 1,5-cyclooctanedithiol, 4-hexyl-1,2-cyclohexanedithiol, p-menthane-2,9-dithiol, and the like.

Other illustrative cycloaliphatic polythiols (e.g., dithiols) useful in this disclosure include, for example, 1,4-cyclohexanedithiol, 1,2-cyclohexanedithiol, and the like, or a combination of those.

Illustrative ether-, ester- or acid-containing polythiols include, for example, 2-mercaptoethyl ether, 2,2'-(ethylenedioxy)diethanethiol, hexa(ethylene glycol)dithiol, trimethylolpropane tris(3-mercaptopropionate), pentaerythritol tetrakis(3-mercaptopropionate), and the like.

Illustrative heteroatom-containing polythiols include, for example, 2-thizoline-2-thiol, 2-mercaptobenzothiazole, 5-methoxylbenzoxazole-2-thiol, 5-phenyl-1H-1,2,4-trizole-3-thiol, 1H-1,24-trizole-3-thiol, 5-phenyl-1,3,4-oxadiazole-2-thiol, 2-thiazoline-2-thiol, 2-mercaptobenzothiazole, 5-methoxybenzoxazole-2-thiol, 4-phenylimidazole-2-thiol, 2-mercaptoimidazole, 1H-1,2,4-trizole-3-thiol, 5-phenyl-1, 3,4-oxadiazole-2-thiol 1,3,4-thiodizole-2,5-dithiol, 1,2,4-thiadiazole-3,5-dithiol, and the like.

The compositions of this disclosure have a kinematic viscosity at a temperature of 100° C. ($Kv_{100}$), measured according to ASTM standard D-445, from about 2 to about 300 cst, preferably from about 2.1 to about 250 cst, and more preferably from about 2.2 to about 200 cst.

The compositions of this disclosure have a kinematic viscosity at a temperature of 40° C. ($Kv_{40}$), measured according to ASTM standard D-445, from about 5 to about 4000 cst, preferably from about 10 to about 3000 cst, and more preferably from about 20 to about 2000 cst.

The compositions of this disclosure have a viscosity index (VI), measured according to ASTM standard D-2270, from about −100 to about 300, preferably from about 0 to about 280, and more preferably from about 50 to about 250.

The compositions of this disclosure have a Noack volatility of no greater than 90 percent, preferably no greater than 80 percent, and more preferably no greater than about 50 percent. As used herein, Noack volatility is determined by ASTM D-5800.

Illustrative compositions of this disclosure include, for example, compositions that result from selective coupling of an olefin with a thiol or polythiol to form sulfur-containing compounds. The compositions of this disclosure contain one or more sulfur-containing compounds.

In particular, the compositions of this disclosure include, for example, (i) the reaction product of one or more aliphatic olefins with one or more aliphatic thiols, aromatic thiols, cycloaliphatic thiols, ether-, ester- or acid-containing thiols, or heteroatom-containing thiols, (ii) the reaction product of one or more aliphatic olefins with one or more aliphatic polythiols, aromatic polythiols, cycloaliphatic polythiols, ether-, ester- or acid-containing polythiols, or heteroatom-containing polythiols, (iii) the reaction product of one or more aromatic olefins with one or more aliphatic thiols, aromatic thiols, cycloaliphatic thiols, ether-, ester- or acid-containing thiols, or heteroatom-containing thiols, (iv) the reaction product of one or more aromatic olefins with one or more aliphatic polythiols, aromatic polythiols, cycloaliphatic polythiols, ether-, ester- or acid-containing polythiols, or heteroatom-containing polythiols, (v) the reaction product of one or more cycloaliphatic olefins with one or more aliphatic thiols, aromatic thiols, cycloaliphatic thiols, ether-, ester- or acid-containing thiols, or heteroatom-containing thiols, and (vi) the reaction product of one or more cycloaliphatic olefins with one or more aliphatic polythiols, aromatic polythiols, cycloaliphatic polythiols, ether-, ester- or acid-containing polythiols, or heteroatom-containing polythiols.

The compositions of this disclosure can be prepared by a process that involves reacting an olefin (e.g., an aliphatic olefin, an aromatic olefin, and/or a cycloaliphatic olefin) with a thiol (e.g., an aliphatic thiol, an aromatic thiol, a cycloaliphatic thiol, an ether-, ester- or acid-containing thiol, and/or a heteroatom-containing thiol) or polythiol (e.g., an aliphatic polythiol, aromatic polythiol, cycloaliphatic polythiol, an ether-, ester- or acid-containing polythiol, and/or a heteroatom-containing polythiol). The reaction is carried out optionally in the presence of a catalyst. The reaction is also carried out under reaction conditions sufficient to produce the composition.

Suitable olefins, thiols and polythiols useful in the process of this disclosure are described herein.

Illustrative catalysts that optionally can be used in the process of this disclosure include, for example, free-radical initiators for olefin-thiol reactions, and the like. Other suitable catalysts include, for example, free-radical initiators that can be used for olefin-thiol reactions. The free radical initiators are well known to those skilled in the art. Illustrative initiators include, but are not limited to, organic peroxides, such as alkyl peroxides, dialkyl peroxides, aroyl peroxides and peroxy esters, and azo compounds. Preferred alkyl hydroperoxides include tertiary-butyl hydroperoxide, tertiary-octyl hydroperoxide and cumene hydroperoxide; preferred dialkyl peroxides include ditertiary-butyl peroxide, 2,5-dimethyl-2,5-di(t-butylperoxy)hexane and di-cumyl peroxide; preferred aroyl peroxides include benzoyl peroxide; preferred peroxy esters include tertiary-butyl peroxypivalate, t-butylperoxy-2-ethylhexanoate (Trigonox 21®) and tertiary-butyl-perbenzoate; and preferred azo compounds include azo-bis-isobutyronitrile. Free radical initiators with an appropriate half-life at reaction temperatures ranging from about −10° C. to about 300° C. can be used. Of these, t-butyl peroxypivalate, t-butylperoxy-2-ethylhexanoate (Trigonox 21®) and t-butyl peroxide are most preferred. The catalyst can be used in conventional amounts needed to catalyze the reaction of the polyalphaolefin oligomer or alpha olefin and the end-functionalized alkane.

Reaction conditions for the reaction of the olefin with the thiol or polythiol (i.e., thiol-ene reaction conditions), such as temperature, pressure and contact time, may also vary greatly and any suitable combination of such conditions may be employed herein. The reaction temperature may range between about −10° C. to about 250° C., and preferably between about 0° C. to about 200° C., and more preferably between about 25° C. to about 150° C. Normally the reaction is carried out under ambient pressure and the contact time may vary from a matter of seconds or minutes to a few hours or greater. The reactants can be added to the reaction mixture or combined in any order. The stir time employed can range from about 0.5 to about 72 hours, preferably from about 1 to 36 hours, and more preferably from about 2 to 24 hours.

Examples of techniques that can be employed to characterize the compositions formed by the process described above include, but are not limited to, analytical gas chromatography, FTIR spectroscopy, nuclear magnetic resonance, thermogravimetric analysis (TGA), inductively coupled plasma mass spectrometry, differential scanning calorimetry (DSC), volatility and viscosity measurements.

This disclosure provides lubricating oils useful as engine oils and in other applications characterized by excellent solvency and dispersancy characteristics. The lubricating oils are based on high quality base stocks including a major portion of a hydrocarbon base fluid such as a PAO or GTL with a secondary cobase stock component which is a sulfur-containing compound as described herein. The lubricating oil base stock can be any oil boiling in the lube oil boiling range, typically between about 100 to 450° C. In the present specification and claims, the terms base oil(s) and base stock(s) are used interchangeably.

The viscosity-temperature relationship of a lubricating oil is one of the critical criteria which must be considered when selecting a lubricant for a particular application. Viscosity Index (VI) is an empirical, unitless number which indicates the rate of change in the viscosity of an oil within a given temperature range. Fluids exhibiting a relatively large change in viscosity with temperature are said to have a low viscosity index. A low VI oil, for example, will thin out at elevated temperatures faster than a high VI oil. Usually, the high VI oil is more desirable because it has higher viscosity at higher temperature, which translates into better or thicker lubrication film and better protection of the contacting machine elements.

In another aspect, as the oil operating temperature decreases, the viscosity of a high VI oil will not increase as much as the viscosity of a low VI oil. This is advantageous because the excessive high viscosity of the low VI oil will decrease the efficiency of the operating machine. Thus high VI (HVI) oil has performance advantages in both high and low temperature operation. VI is determined according to ASTM method D 2270-93 [1998]. VI is related to kinematic viscosities measured at 40° C. and 100° C. using ASTM Method D 445-01.

Lubricating Oil Base Stocks

A wide range of lubricating oils is known in the art. Lubricating oils that are useful in the present disclosure are both natural oils and synthetic oils. Natural and synthetic oils (or mixtures thereof) can be used unrefined, refined, or rerefined (the latter is also known as reclaimed or reprocessed oil). Unrefined oils are those obtained directly from a natural or synthetic source and used without added purification. These include shale oil obtained directly from retorting operations, petroleum oil obtained directly from primary distillation, and ester oil obtained directly from an esterification process. Refined oils are similar to the oils discussed for unrefined oils except refined oils are subjected to one or more purification steps to improve the at least one lubricating oil property. One skilled in the art is familiar with many purification processes. These processes include solvent extraction, secondary distillation, acid extraction, base extraction, filtration, and percolation. Rerefined oils are obtained by processes analogous to refined oils but using an oil that has been previously used as a feed stock.

Groups I, II, III, IV and V are broad categories of base oil stocks developed and defined by the American Petroleum Institute (API Publication 1509; www.API.org) to create guidelines for lubricant base oils. Group I base stocks generally have a viscosity index of between about 80 to 120 and contain greater than about 0.03% sulfur and less than about 90% saturates. Group II base stocks generally have a viscosity index of between about 80 to 120, and contain less than or equal to about 0.03% sulfur and greater than or equal to about 90% saturates. Group III stock generally has a viscosity index greater than about 120 and contains less than or equal to about 0.03% sulfur and greater than about 90% saturates. Group IV includes polyalphaolefins (PAO). Group V base stocks include base stocks not included in Groups I-IV. The table below summarizes properties of each of these five groups.

| | Base Oil Properties | | |
|---|---|---|---|
| | Saturates | Sulfur | Viscosity Index |
| Group I | <90 and/or | >0.03% and | ≥80 and <120 |
| Group II | ≥90 and | ≤0.03% and | ≥80 and <120 |
| Group III | ≥90 and | ≤0.03% and | ≥120 |
| Group IV | Includes polyalphaolefins (PAO) products | | |
| Group V | All other base oil stocks not included in Groups I, II, III or IV | | |

Natural oils include animal oils, vegetable oils (castor oil and lard oil, for example), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale are also useful in the present disclosure. Natural oils vary also as to the method used for their production and purification, for example, their distillation range and whether they are straight run or cracked, hydrorefined, or solvent extracted.

Group II and/or Group III hydroprocessed or hydrocracked base stocks, as well as synthetic oils such as polyalphaolefins, alkyl aromatics and synthetic esters, i.e. Group IV and Group V oils are also well known base stock oils.

Synthetic oils include hydrocarbon oil such as polymerized and interpolymerized olefins (polybutylenes, polypropylenes, propylene isobutylene copolymers, ethylene-olefin copolymers, and ethylene-alphaolefin copolymers, for example). Polyalphaolefin (PAO) oil base stocks, the Group IV API base stocks, are a commonly used synthetic hydrocarbon oil. By way of example, PAOs derived from $C_8$, $C_{10}$, $C_{12}$, $C_{14}$ olefins or mixtures thereof may be utilized. See U.S. Pat. Nos. 4,956,122; 4,827,064; and 4,827,073, which are incorporated herein by reference in their entirety. Group IV oils, that is, the PAO base stocks have viscosity indices preferably greater than 130, more preferably greater than 135, still more preferably greater than 140.

Esters in a minor amount may be useful in the lubricating oils of this disclosure. Additive solvency and seal compatibility characteristics may be secured by the use of esters such as the esters of dibasic acids with monoalkanols and the polyol esters of monocarboxylic acids. Esters of the former type include, for example, the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc.

Particularly useful synthetic esters are those which are obtained by reacting one or more polyhydric alcohols, preferably the hindered polyols such as the neopentyl polyols; e.g., neopentyl glycol, trimethylol ethane, 2-methyl-2-propyl-1,3-propanediol, trimethylol propane, pentaerythritol and dipentaerythritol with alkanoic acids containing at least about 4 carbon atoms, preferably $C_5$ to $C_{30}$ acids such as saturated straight chain fatty acids including caprylic acid, capric acids, lauric acid, myristic acid, palmitic acid, stearic acid, arachic acid, and behenic acid, or the corresponding branched chain fatty acids or unsaturated fatty acids such as oleic acid, or mixtures of any of these materials.

Esters should be used in a amount such that the improved wear and corrosion resistance provided by the lubricating oils of this disclosure are not adversely affected.

Non-conventional or unconventional base stocks and/or base oils include one or a mixture of base stock(s) and/or base oil(s) derived from: (1) one or more Gas-to-Liquids (GTL) materials, as well as (2) hydrodewaxed, or hydroisomerized/cat (and/or solvent) dewaxed base stock(s) and/or base oils derived from synthetic wax, natural wax or waxy feeds, mineral and/or non-mineral oil waxy feed stocks such as gas oils, slack waxes (derived from the solvent dewaxing of natural oils, mineral oils or synthetic oils; e.g., Fischer-Tropsch feed stocks), natural waxes, and waxy stocks such as gas oils, waxy fuels hydrocracker bottoms, waxy raffinate, hydrocrackate, thermal crackates, foots oil or other mineral, mineral oil, or even non-petroleum oil derived waxy materials such as waxy materials recovered from coal liquefaction or shale oil, linear or branched hydrocarbyl compounds with carbon number of about 20 or greater, preferably about 30 or greater and mixtures of such base stocks and/or base oils.

GTL materials are materials that are derived via one or more synthesis, combination, transformation, rearrangement, and/or degradation/deconstructive processes from gaseous carbon-containing compounds, hydrogen-containing compounds and/or elements as feed stocks such as hydrogen, carbon dioxide, carbon monoxide, water, methane, ethane, ethylene, acetylene, propane, propylene, propyne, butane, butylenes, and butynes. GTL base stocks and/or base oils are GTL materials of lubricating viscosity that are generally derived from hydrocarbons; for example, waxy synthesized hydrocarbons, that are themselves derived from simpler gaseous carbon-containing compounds, hydrogen-containing compounds and/or elements as feed stocks. GTL base stock(s) and/or base oil(s) include oils boiling in the lube oil boiling range (1) separated/fractionated from synthesized GTL materials such as, for example, by distillation and subsequently subjected to a final wax processing step which involves either or both of a catalytic dewaxing process, or a solvent dewaxing process, to produce lube oils of reduced/low pour point; (2) synthesized wax isomerates, comprising, for example, hydrodewaxed or hydroisomerized cat and/or solvent dewaxed synthesized wax or waxy hydrocarbons; (3) hydrodewaxed or hydroisomerized cat and/or solvent dewaxed Fischer-Tropsch (F-T) material (i.e., hydrocarbons, waxy hydrocarbons, waxes and possible analogous oxygenates); preferably hydrodewaxed or hydroisomerized/followed by cat and/or solvent dewaxing dewaxed F-T waxy hydrocarbons, or hydrodewaxed or hydroisomerized/followed by cat (or solvent) dewaxing dewaxed, F-T waxes, or mixtures thereof.

GTL base stock(s) and/or base oil(s) derived from GTL materials, especially, hydrodewaxed or hydroisomerized/followed by cat and/or solvent dewaxed wax or waxy feed, preferably F-T material derived base stock(s) and/or base oil(s), are characterized typically as having kinematic viscosities at 100° C. of from about 2 mm$^2$/s to about 50 mm$^2$/s (ASTM D445). They are further characterized typically as having pour points of −5° C. to about −40° C. or lower (ASTM D97). They are also characterized typically as having viscosity indices of about 80 to about 140 or greater (ASTM D2270).

In addition, the GTL base stock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stock(s) and/or base oil(s) typically have very low sulfur and nitrogen content, generally containing less than about 10 ppm, and more typically less than about 5 ppm of each of these elements. The sulfur and nitrogen content of GTL base stock(s) and/or base oil(s) obtained from F-T material, especially F-T wax, is essentially nil. In addition, the absence of phosphorous and aromatics make this materially especially suitable for the formulation of low SAP products.

The term GTL base stock and/or base oil and/or wax isomerate base stock and/or base oil is to be understood as embracing individual fractions of such materials of wide viscosity range as recovered in the production process, mixtures of two or more of such fractions, as well as mixtures of one or two or more low viscosity fractions with one, two or more higher viscosity fractions to produce a blend wherein the blend exhibits a target kinematic viscosity.

The GTL material, from which the GTL base stock(s) and/or base oil(s) is/are derived is preferably an F-T material (i.e., hydrocarbons, waxy hydrocarbons, wax).

Base oils for use in the formulated lubricating oils useful in the present disclosure are any of the variety of oils corresponding to API Group I, Group II, Group III, Group IV, Group V and Group VI oils and mixtures thereof, preferably API Group II, Group III, Group IV, Group V and Group VI oils and mixtures thereof, more preferably the Group III to Group VI base oils due to their exceptional volatility, stability, viscometric and cleanliness features. Minor quantities of Group I stock, such as the amount used to dilute additives for blending into formulated lube oil products, can be tolerated but should be kept to a minimum, i.e. amounts only associated with their use as diluent/carrier oil for additives used on an "as received" basis. Even in regard to the Group II stocks, it is preferred that the Group II stock be in the higher quality range associated with that stock, i.e. a Group II stock having a viscosity index in the range 100<VI<120.

In addition, the GTL base stock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stock(s) and/or base oil(s) and hydrodewaxed, or hydroisomerized/cat (and/or solvent) dewaxed base stock(s) and/or base oil(s) typically have very low sulfur and nitrogen content, generally containing less than about 10 ppm, and more typically less than about 5 ppm of each of these elements. The sulfur and nitrogen content of GTL base stock(s) and/or base oil(s) obtained from F-T material, especially F-T wax, is essentially nil. In addition, the absence of phosphorous and aromatics make this material especially suitable for the formulation of low sulfur, sulfated ash, and phosphorus (low SAP) products.

The basestock component of the present lubricating oils will typically be from 50 to 99 weight percent of the total composition (all proportions and percentages set out in this specification are by weight unless the contrary is stated) and more usually in the range of 80 to 99 weight percent.

Cobase Stock Components

Sulfur-containing cobase stock components useful in this disclosure include, for example, compositions containing one or more sulfur-containing compounds represented by the formula

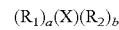
$(R_1)_a(X)(R_2)_b$ wherein $R_1$ and $R_2$ are the same or different and are the residue of an olefin having from about 4 to about 40 carbon atoms, X is the residue of a thiol or polythiol, $\underline{a}$ is a value from 1 to about 6, and $\underline{b}$ is a value from 0 to about 6. The olefin is selected from the group consisting of an aliphatic olefin, an aromatic olefin, and a cycloaliphatic olefin. The thiol is selected from the group consisting of an aliphatic thiol, an aromatic thiol, a cycloaliphatic thiol, an ether-, ester- or acid-containing thiol, and a heteroatom-containing thiol. The polythiol is selected from the group consisting of an aliphatic polythiol, an aromatic polythiol, a cycloaliphatic polythiol, an ether-, ester- or acid-containing polythiol, and a heteroatom-containing polythiol.

The compositions have a kinematic viscosity at a temperature of 100° C. ($Kv_{100}$), measured according to ASTM standard D-445, from about 2 to about 300 cst, a kinematic viscosity at a temperature of 40° C. ($Kv_{40}$), measured according to ASTM standard D-445, from about 5 to about 4000 cst, a viscosity index (VI), measured according to ASTM standard D-2270, from about −100 to about 300, and a Noack volatility, measured according to ASTM D-5800, of no greater than about 90 percent.

Illustrative cobase stock components useful in this disclosure include, for example, compositions that result from selective coupling of an olefin with a thiol or polythiol to form sulfur-containing compounds as described herein. The cobase stock components useful in this disclosure comprise compositions containing one or more sulfur-containing compounds.

Methods for the production of sulfur-containing cobase stock components suitable for use in the present disclosure are described herein. For example, an olefin (e.g., an aliphatic olefin, an aromatic olefin, and/or a cycloaliphatic olefin) can be reacted with a thiol (e.g., an aliphatic thiol, an aromatic thiol, a cycloaliphatic thiol, an ether-, ester- or acid-containing thiol, and/or a heteroatom-containing thiol) or polythiol (e.g., an aliphatic polythiol, aromatic polythiol, cycloaliphatic polythiol, an ether-, ester- or acid-containing polythiol, and/or a heteroatom-containing polythiol). The reaction is carried out optionally in the presence of a catalyst. The reaction is carried out under reaction conditions sufficient to produce the sulfur-containing cobase stock as more fully described herein.

The sulfur-containing cobase stock component is preferably present in an amount sufficient for providing solubility and dispersancy of polar additives and/or sludge in the lubricating oil. The sulfur-containing cobase stock component is present in the lubricating oils of this disclosure in an amount from about 1 to about 50 weight percent, preferably from about 5 to about 30 weight percent, and more preferably from about 10 to about 20 weight percent.

Other Additives

The formulated lubricating oil useful in the present disclosure may additionally contain one or more of the other commonly used lubricating oil performance additives including but not limited to dispersants, other detergents, corrosion inhibitors, rust inhibitors, metal deactivators, other anti-wear agents and/or extreme pressure additives, anti-seizure agents, wax modifiers, viscosity index improvers, viscosity modifiers, fluid-loss additives, seal compatibility agents, other friction modifiers, lubricity agents, anti-staining agents, chromophoric agents, defoamants, demulsifiers, emulsifiers, densifiers, wetting agents, gelling agents, tackiness agents, colorants, and others. For a review of many commonly used additives, see Klamann in Lubricants and Related Products, Verlag Chemie, Deerfield Beach, Fla.; ISBN 0-89573-177-0. Reference is also made to "Lubricant Additives Chemistry and Applications" edited by Leslie R. Rudnick, Marcel Dekker, Inc. New York, 2003 ISBN: 0-8247-0857-1.

The types and quantities of performance additives used in combination with the instant disclosure in lubricant compositions are not limited by the examples shown herein as illustrations.

Viscosity Improvers

Viscosity improvers (also known as Viscosity Index modifiers, and VI improvers) increase the viscosity of the oil composition at elevated temperatures which increases film thickness, while having limited effect on viscosity at low temperatures.

Suitable viscosity improvers include high molecular weight hydrocarbons, polyesters and viscosity index improver dispersants that function as both a viscosity index improver and a dispersant. Typical molecular weights of these polymers are between about 10,000 to 1,000,000, more typically about 20,000 to 500,000, and even more typically between about 50,000 and 200,000.

Examples of suitable viscosity improvers are polymers and copolymers of methacrylate, butadiene, olefins, or alkylated styrenes. Polyisobutylene is a commonly used viscosity index improver. Another suitable viscosity index improver is polymethacrylate (copolymers of various chain length alkyl methacrylates, for example), some formulations of which also serve as pour point depressants. Other suitable viscosity index improvers include copolymers of ethylene and propylene, hydrogenated block copolymers of styrene and isoprene, and polyacrylates (copolymers of various chain length acrylates, for example). Specific examples include styrene-isoprene or styrene-butadiene based polymers of 50,000 to 200,000 molecular weight.

The amount of viscosity modifier may range from zero to 8 wt %, preferably zero to 4 wt %, more preferably zero to 2 wt % based on active ingredient and depending on the specific viscosity modifier used.

Antioxidants

Typical antioxidant include phenolic antioxidants, aminic antioxidants and oil-soluble copper complexes.

The phenolic antioxidants include sulfurized and non-sulfurized phenolic antioxidants. The terms "phenolic type" or "phenolic antioxidant" used herein includes compounds having one or more than one hydroxyl group bound to an aromatic ring which may itself be mononuclear, e.g., benzyl, or poly-nuclear, e.g., naphthyl and spiro aromatic compounds. Thus "phenol type" includes phenol per se, catechol, resorcinol, hydroquinone, naphthol, etc., as well as alkyl or alkenyl and sulfurized alkyl or alkenyl derivatives thereof, and bisphenol type compounds including such bi-phenol compounds linked by alkylene bridges sulfuric bridges or oxygen bridges. Alkyl phenols include mono- and poly-alkyl or alkenyl phenols, the alkyl or alkenyl group containing from about 3-100 carbons, preferably 4 to 50 carbons and sulfurized derivatives thereof, the number of alkyl or alkenyl groups present in the aromatic ring ranging from 1 to up to the available unsatisfied valences of the aromatic ring remaining after counting the number of hydroxyl groups bound to the aromatic ring.

Generally, therefore, the phenolic antioxidant may be represented by the general formula:

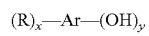

where Ar is selected from the group consisting of:

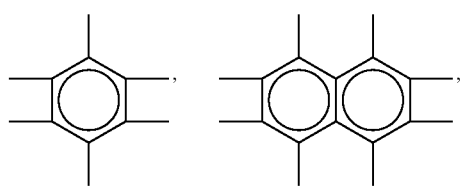

-continued

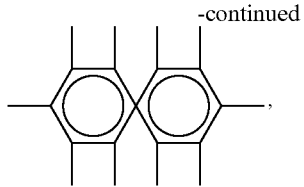

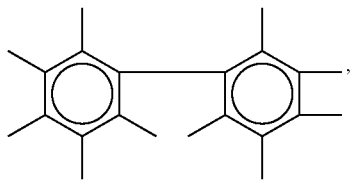

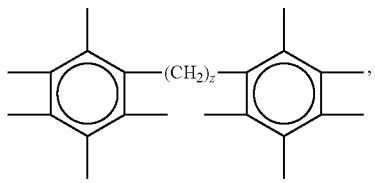

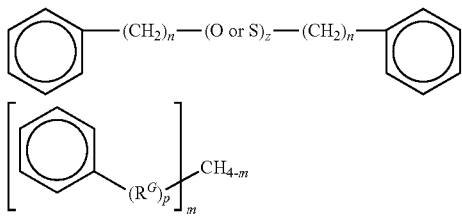

wherein R is a $C_3$-$C_{100}$ alkyl or alkenyl group, a sulfur substituted alkyl or alkenyl group, preferably a $C_4$-$C_{50}$ alkyl or alkenyl group or sulfur substituted alkyl or alkenyl group, more preferably $C_3$-$C_{100}$ alkyl or sulfur substituted alkyl group, most preferably a $C_4$-$C_{50}$ alkyl group, $R^G$ is a $C_1$-$C_{100}$ alkylene or sulfur substituted alkylene group, preferably a $C_2$-$C_{50}$ alkylene or sulfur substituted alkylene group, more preferably a $C_2$-$C_2$ alkylene or sulfur substituted alkylene group, y is at least 1 to up to the available valences of Ar, x ranges from 0 to up to the available valances of Ar-y, z ranges from 1 to 10, n ranges from 0 to 20, and m is 0 to 4 and p is 0 or 1, preferably y ranges from 1 to 3, x ranges from 0 to 3, z ranges from 1 to 4 and n ranges from 0 to 5, and p is 0.

Preferred phenolic antioxidant compounds are the hindered phenolics and phenolic esters which contain a sterically hindered hydroxyl group, and these include those derivatives of dihydroxy aryl compounds in which the hydroxyl groups are in the o- or p-position to each other. Typical phenolic antioxidants include the hindered phenols substituted with $C_1$+ alkyl groups and the alkylene coupled derivatives of these hindered phenols. Examples of phenolic materials of this type 2-t-butyl-4-heptyl phenol; 2-t-butyl-4-octyl phenol; 2-t-butyl-4-dodecyl phenol; 2,6-di-t-butyl-4-heptyl phenol; 2,6-di-t-butyl-4-dodecyl phenol; 2-methyl-6-t-butyl-4-heptyl phenol; 2-methyl-6-t-butyl-4-dodecyl phenol; 2,6-di-t-butyl-4 methyl phenol; 2,6-di-t-butyl-4-ethyl phenol; and 2,6-di-t-butyl 4 alkoxy phenol; and

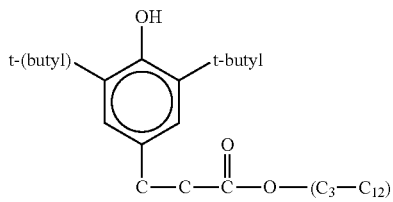

Phenolic type antioxidants are well known in the lubricating industry and commercial examples such as Ethanox® 4710, Irganox® 1076, Irganox® L1035, Irganox® 1010, Irganox® L109, Irganox® L118, Irganox® L135 and the like are familiar to those skilled in the art. The above is presented only by way of exemplification, not limitation on the type of phenolic antioxidants which can be used.

The phenolic antioxidant can be employed in an amount in the range of about 0.1 to 3 wt %, preferably about 1 to 3 wt %, more preferably 1.5 to 3 wt % on an active ingredient basis.

Aromatic amine antioxidants include phenyl-α-naphthyl amine which is described by the following molecular structure:

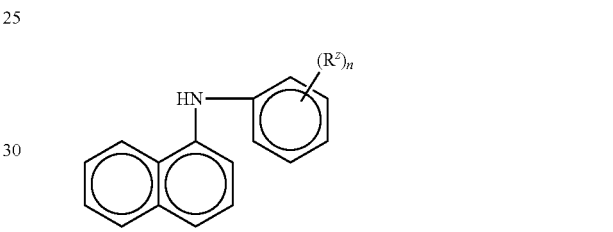

wherein $R^z$ is hydrogen or a $C_1$ to $C_{14}$ linear or $C_3$ to $C_{14}$ branched alkyl group, preferably $C_1$ to $C_{10}$ linear or $C_3$ to $C_{10}$ branched alkyl group, more preferably linear or branched $C_6$ to $C_8$ and n is an integer ranging from 1 to 5 preferably 1. A particular example is Irganox L06.

Other aromatic amine antioxidants include other alkylated and non-alkylated aromatic amines such as aromatic monoamines of the formula $R^8R^9R^{10}N$ where $R^8$ is an aliphatic, aromatic or substituted aromatic group, $R^9$ is an aromatic or a substituted aromatic group, and $R^{10}$ is H, alkyl, aryl or $R^{11}S(O)_xR^{12}$ where $R^{11}$ is an alkylene, alkenylene, or aralkylene group, $R^{12}$ is a higher alkyl group, or an alkenyl, aryl, or alkaryl group, and x is 0, 1 or 2. The aliphatic group $R^8$ may contain from 1 to about 20 carbon atoms, and preferably contains from about 6 to 12 carbon atoms. The aliphatic group is a saturated aliphatic group. Preferably, both $R^8$ and $R^9$ are aromatic or substituted aromatic groups, and the aromatic group may be a fused ring aromatic group such as naphthyl. Aromatic groups $R^8$ and $R^9$ may be joined together with other groups such as S.

Typical aromatic amines antioxidants have alkyl substituent groups of at least about 6 carbon atoms. Examples of aliphatic groups include hexyl, heptyl, octyl, nonyl, and decyl. Generally, the aliphatic groups will not contain more than about 14 carbon atoms. The general types of such other additional amine antioxidants which may be present include diphenylamines, phenothiazines, imidodibenzyls and diphenyl phenylene diamines. Mixtures of two or more of such other additional aromatic amines may also be present. Polymeric amine antioxidants can also be used.

Another class of antioxidant used in lubricating oil compositions and which may also be present are oil-soluble copper compounds. Any oil-soluble suitable copper compound may be blended into the lubricating oil. Examples of suitable copper antioxidants include copper dihydrocarbyl thio- or dithio-phosphates and copper salts of carboxylic acid (naturally occurring or synthetic). Other suitable copper salts include copper dithiacarbamates, sulphonates, phenates, and acetylacetonates. Basic, neutral, or acidic copper Cu(I) and or Cu(II) salts derived from alkenyl succinic acids or anhydrides are known to be particularly useful.

Such antioxidants may be used individually or as mixtures of one or more types of antioxidants, the total amount employed being an amount of about 0.50 to 5 wt %, preferably about 0.75 to 3 wt % (on an as-received basis).

Detergents

In addition to the alkali or alkaline earth metal salicylate detergent which is an essential component in the present disclosure, other detergents may also be present. While such other detergents can be present, it is preferred that the amount employed be such as to not interfere with the synergistic effect attributable to the presence of the salicylate. Therefore, most preferably such other detergents are not employed.

If such additional detergents are present, they can include alkali and alkaline earth metal phenates, sulfonates, carboxylates, phosphonates and mixtures thereof. These supplemental detergents can have total base number (TBN) ranging from neutral to highly overbased, i.e. TBN of 0 to over 500, preferably 2 to 400, more preferably 5 to 300, and they can be present either individually or in combination with each other in an amount in the range of from 0 to 10 wt %, preferably 0.5 to 5 wt % (active ingredient) based on the total weight of the formulated lubricating oil. As previously stated, however, it is preferred that such other detergent not be present in the formulation.

Such additional other detergents include by way of example and not limitation calcium phenates, calcium sulfonates, magnesium phenates, magnesium sulfonates and other related components (including borated detergents).

Dispersants

During engine operation, oil-insoluble oxidation byproducts are produced. Dispersants help keep these byproducts in solution, thus diminishing their deposition on metal surfaces. Dispersants may be ashless or ash-forming in nature. Preferably, the dispersant is ashless. So called ashless dispersants are organic materials that form substantially no ash upon combustion. For example, non-metal-containing or borated metal-free dispersants are considered ashless. In contrast, metal-containing detergents discussed above form ash upon combustion.

Suitable dispersants typically contain a polar group attached to a relatively high molecular weight hydrocarbon chain. The polar group typically contains at least one element of nitrogen, oxygen, or phosphorus. Typical hydrocarbon chains contain 50 to 400 carbon atoms.

A particularly useful class of dispersants are the alkenylsuccinic derivatives, typically produced by the reaction of a long chain substituted alkenyl succinic compound, usually a substituted succinic anhydride, with a polyhydroxy or polyamino compound. The long chain group constituting the oleophilic portion of the molecule which confers solubility in the oil, is normally a polyisobutylene group. Many examples of this type of dispersant are well known commercially and in the literature. Exemplary patents describing such dispersants are U.S. Pat. Nos. 3,172,892; 3,219,666; 3,316,177 and 4,234,435. Other types of dispersants are described in U.S. Pat. No. 3,036,003; and U.S. Pat. No. 5,705,458.

Hydrocarbyl-substituted succinic acid compounds are popular dispersants. In particular, succinimide, succinate esters, or succinate ester amides prepared by the reaction of a hydrocarbon-substituted succinic acid compound preferably having at least 50 carbon atoms in the hydrocarbon substituent, with at least one equivalent of an alkylene amine are particularly useful.

Succinimides are formed by the condensation reaction between alkenyl succinic anhydrides and amines. Molar ratios can vary depending on the amine or polyamine. For example, the molar ratio of alkenyl succinic anhydride to TEPA can vary from about 1:1 to about 5:1.

Succinate esters are formed by the condensation reaction between alkenyl succinic anhydrides and alcohols or polyols. Molar ratios can vary depending on the alcohol or polyol used. For example, the condensation product of an alkenyl succinic anhydride and pentaerythritol is a useful dispersant.

Succinate ester amides are formed by condensation reaction between alkenyl succinic anhydrides and alkanol amines. For example, suitable alkanol amines include ethoxylated polyalkylpolyamines, propoxylated polyalkylpolyamines and polyalkenylpolyamines such as polyethylene polyamines. One example is propoxylated hexamethylenediamine.

The molecular weight of the alkenyl succinic anhydrides will typically range between 800 and 2,500. The above products can be post-reacted with various reagents such as sulfur, oxygen, formaldehyde, carboxylic acids such as oleic acid, and boron compounds such as borate esters or highly borated dispersants. The dispersants can be borated with from about 0.1 to about 5 moles of boron per mole of dispersant reaction product.

Mannich base dispersants are made from the reaction of alkylphenols, formaldehyde, and amines. Process aids and catalysts, such as oleic acid and sulfonic acids, can also be part of the reaction mixture. Molecular weights of the alkylphenols range from 800 to 2,500.

Typical high molecular weight aliphatic acid modified Mannich condensation products can be prepared from high molecular weight alkyl-substituted hydroxyaromatics or $HN(R)_2$ group-containing reactants.

Examples of high molecular weight alkyl-substituted hydroxyaromatic compounds are polypropylphenol, polybutylphenol, and other polyalkylphenols. These polyalkylphenols can be obtained by the alkylation, in the presence of an alkylating catalyst, such as $BF_3$, of phenol with high molecular weight polypropylene, polybutylene, and other polyalkylene compounds to give alkyl substituents on the benzene ring of phenol having an average 600-100,000 molecular weight.

Examples of $HN(R)_2$ group-containing reactants are alkylene polyamines, principally polyethylene polyamines. Other representative organic compounds containing at least one $HN(R)_2$ group suitable for use in the preparation of Mannich condensation products are well known and include the mono- and di-amino alkanes and their substituted analogs, e.g., ethylamine and diethanol amine; aromatic diamines, e.g., phenylene diamine, diamino naphthalenes; heterocyclic amines, e.g., morpholine, pyrrole, pyrrolidine, imidazole, imidazolidine, and piperidine; melamine and their substituted analogs.

Examples of alkylene polyamine reactants include ethylenediamine, diethylene triamine, triethylene tetraamine, tetraethylene pentaamine, pentaethylene hexamine, hexaethylene heptaamine, heptaethylene octaamine, octaethylene nonaamine, nonaethylene decamine, and decaethylene undecamine and mixture of such amines having nitrogen contents corresponding to the alkylene polyamines, in the formula $H_2N$—$(Z$—$NH$—$)_nH$, mentioned before, Z is a divalent ethylene and n is 1 to 10 of the foregoing formula. Corresponding propylene polyamines such as propylene diamine and di-, tri-, tetra-, pentapropylene tri-, tetra-, penta- and hexaamines are also suitable reactants. The alkylene polyamines are usually obtained by the reaction of ammonia and dihalo alkanes, such as dichloro alkanes. Thus the alkylene polyamines obtained from the reaction of 2 to 11 moles of ammonia with 1 to 10 moles of dichloroalkanes having 2 to 6 carbon atoms and the chlorines on different carbons are suitable alkylene polyamine reactants.

Aldehyde reactants useful in the preparation of the high molecular products useful in this disclosure include the aliphatic aldehydes such as formaldehyde (also as paraformaldehyde and formalin), acetaldehyde and aldol (β-hydroxybutyraldehyde). Formaldehyde or a formaldehyde-yielding reactant is preferred.

Preferred dispersants include borated and non-borated succinimides, including those derivatives from mono-succinimides, bis-succinimides, and/or mixtures of mono- and bis-succinimides, wherein the hydrocarbyl succinimide is derived from a hydrocarbylene group such as polyisobutylene having a Mn of from about 500 to about 5000 or a mixture of such hydrocarbylene groups. Other preferred dispersants include succinic acid-esters and amides, alkylphenol-polyamine-coupled Mannich adducts, their capped derivatives, and other related components. Such additives may be used in an amount of about 0.1 to 20 wt %, preferably about 0.1 to 8 wt %, more preferably about 1 to 6 wt % (on an as-received basis) based on the weight of the total lubricant.

Pour Point Depressants

Conventional pour point depressants (also known as lube oil flow improvers) may also be present. Pour point depressant may be added to lower the minimum temperature at which the fluid will flow or can be poured. Examples of suitable pour point depressants include alkylated naphthalenes polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. Such additives may be used in amount of about 0.0 to 0.5 wt %, preferably about 0 to 0.3 wt %, more preferably about 0.001 to 0.1 wt % on an as-received basis.

Corrosion Inhibitors/Metal Deactivators

Corrosion inhibitors are used to reduce the degradation of metallic parts that are in contact with the lubricating oil composition. Suitable corrosion inhibitors include aryl thiazines, alkyl substituted dimercapto thiodiazoles thiadiazoles and mixtures thereof. Such additives may be used in an amount of about 0.01 to 5 wt %, preferably about 0.01 to 1.5 wt %, more preferably about 0.01 to 0.2 wt %, still more preferably about 0.01 to 0.1 wt % (on an as-received basis) based on the total weight of the lubricating oil composition.

Seal Compatibility Additives

Seal compatibility agents help to swell elastomeric seals by causing a chemical reaction in the fluid or physical change in the elastomer. Suitable seal compatibility agents for lubricating oils include organic phosphates, aromatic esters, aromatic hydrocarbons, esters (butylbenzyl phthalate, for example), and polybutenyl succinic anhydride and sulfolane-type seal swell agents such as Lubrizol 730-type seal swell additives. Such additives may be used in an amount of about 0.01 to 3 wt %, preferably about 0.01 to 2 wt % on an as-received basis.

Anti-Foam Agents

Anti-foam agents may advantageously be added to lubricant compositions. These agents retard the formation of stable foams. Silicones and organic polymers are typical anti-foam agents. For example, polysiloxanes, such as silicon oil or polydimethyl siloxane, provide antifoam properties. Anti-foam agents are commercially available and may be used in conventional minor amounts along with other additives such as demulsifiers; usually the amount of these additives combined is less than 1 percent, preferably 0.001 to about 0.5 wt %, more preferably about 0.001 to about 0.2 wt %, still more preferably about 0.0001 to 0.15 wt % (on an as-received basis) based on the total weight of the lubricating oil composition.

Inhibitors and Antirust Additives

Antirust additives (or corrosion inhibitors) are additives that protect lubricated metal surfaces against chemical attack by water or other contaminants. One type of anti-rust additive is a polar compound that wets the metal surface preferentially, protecting it with a film of oil. Another type of anti-rust additive absorbs water by incorporating it in a water-in-oil emulsion so that only the oil touches the surface. Yet another type of anti-rust additive chemically adheres to the metal to produce a non-reactive surface. Examples of suitable additives include zinc dithiophosphates, metal phenolates, basic metal sulfonates, fatty acids and amines. Such additives may be used in an amount of about 0.01 to 5 wt %, preferably about 0.01 to 1.5 wt % on an as-received basis.

In addition to the ZDDP antiwear additives which are essential components of the present disclosure, other antiwear additives can be present, including zinc dithiocarbamates, molybdenum dialkyldithiophosphates, molybdenum dithiocarbamates, other organo molybdenum-nitrogen complexes, sulfurized olefins, etc.

The term "organo molybdenum-nitrogen complexes" embraces the organo molybdenum-nitrogen complexes described in U.S. Pat. No. 4,889,647. The complexes are reaction products of a fatty oil, dithanolamine and a molybdenum source. Specific chemical structures have not been assigned to the complexes. U.S. Pat. No. 4,889,647 reports an infrared spectrum for a typical reaction product of that disclosure; the spectrum identifies an ester carbonyl band at 1740 $cm^{-1}$ and an amide carbonyl band at 1620 $cm^{-1}$. The fatty oils are glyceryl esters of higher fatty acids containing at least 12 carbon atoms up to 22 carbon atoms or more. The molybdenum source is an oxygen-containing compound such as ammonium molybdates, molybdenum oxides and mixtures.

Other organo molybdenum complexes which can be used in the present disclosure are tri-nuclear molybdenum-sulfur compounds described in EP 1 040 115 and WO 99/31113 and the molybdenum complexes described in U.S. Pat. No. 4,978,464.

In the above detailed description, the specific embodiments of this disclosure have been described in connection with its preferred embodiments. However, to the extent that the above description is specific to a particular embodiment or a particular use of this disclosure, this is intended to be illustrative only and merely provides a concise description of the exemplary embodiments. Accordingly, the disclosure is not limited to the specific embodiments described above, but rather, the disclosure includes all alternatives, modifications, and equivalents falling within the true scope of the appended claims. Various modifications and variations of this disclosure will be obvious to a worker skilled in the art and it is to be understood that such modifications and variations are to be included within the purview of this application and the spirit and scope of the claims.

EXAMPLES

Example 1

Reaction of 2-vinyl naphthalene and octanethiol: Synthesis of (2-(naphthalene-2-yl)ethyl)(octyl)sulfane

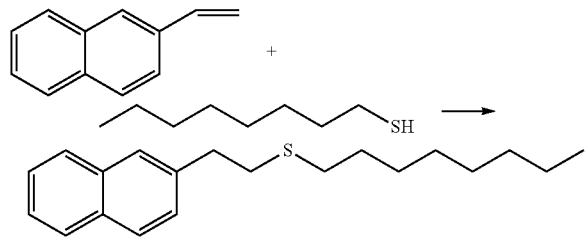

5.0 grams (32.4 mmol, MW: 154.21) 2-vinylnaphthalene, 7.1 grams (48.6 mmol, MW: 146.29) octanethiol and 0.266 grams (1.62 mmol, MW: 164.21) 2,2'-azobis(2-methylpropionitrile) (AIBN) were charged in a 25 milliliter thick sealed glass reactor. After addition, the reaction mixture was stirred for 68 hours at 110° C. The reaction was then stopped and cooled down to room temperature. The excess of unreacted octanethiol was removed by air bath oven at 200° C. under vacuum for 1 hour. The final product was determined by IR, $^1$HNMR. Yields: 8.8 grams. (90%). IR: (cm$^{-1}$) 3052, 3019, 2924, 2853, 1914, 1632, 1600, 1508, 1466, 1376, 1270, 1222, 1145, 1018, 947, 890, 854, 816, 782, 743. $^1$H NMR (CDCl$_3$): 7.77-7.31 (7H, m), 3.03 (2H, t), 2.84 (2H, t), 2.52 (2H, t), 1.58 (2H, m) 1.46-1.27 (10H, m), 0.87 (3H, t).

Example 2

Reaction of 2-vinyl naphthalene and 2-ethylhexylthiol: Synthesis of (2-ethylhexyl)(2-(naphthalene-2-yl)ethyl)sulfane

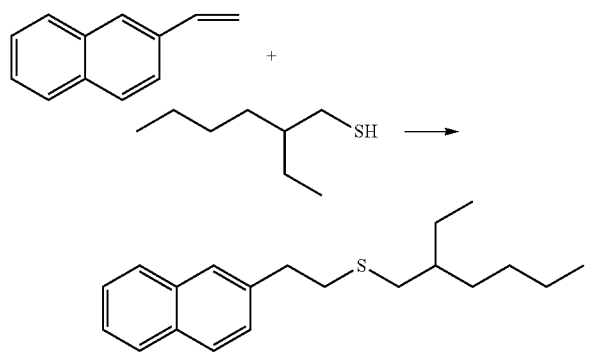

5.0 grams (32.4 mmol, MW: 154.21) 2-vinylnaphthalene, 7.1 grams (48.6 mmol, MW: 146.29) 2-ethylhexylthiol and 0.266 grams (1.62 mmol, MW: 164.21) 2,2'-azobis(2-methylpropionitrile) (AIBN) were charged in a 25 milliliter thick sealed glass reactor. After addition, the reaction mixture was stirred for 18 hours at 115° C. The reaction was then stopped and cooled down to room temperature. The excess of unreacted 2-ethylhexylthiol was removed by air bath oven at 200° C. under vacuum for 1 hour. The final product was determined by IR, 1HNMR. Yields: 8.1 grams. (83%). IR: (cm$^{-1}$) 3052, 2957, 2926, 2870, 2856, 1632, 1600, 1508, 1457, 1378, 1270, 1222, 1169, 1143, 1125, 1018, 658, 891, 854, 816, 783, 742. $^1$H NMR (CDCl$_3$): 7.78-7.34 (7H, m), 3.05 (2H, t), 2.83 (2H, t), 2.53 (2H, t), (1.48-1.27 (10H, m), 0.87 (6H, m).

Example 3

Lube Properties of Base Stocks

The lube properties of the products of Examples 1-7 were evaluated and the data are shown below. The kinematic viscosity (Kv) of the liquid product was measured using ASTM standards D-445 and reported at temperatures of 100° C. (Kv at 100° C.) or 40° C. (Kv at 40° C.). The viscosity index (VI) was measured according to ASTM standard D-2270 using the measured kinematic viscosities for each product. The product volatility was measured using thremogravimetric analysis (TGA) based Noack. Noack volatility was determined by ASTM D-5800.

| Base Stock # | Mol. Wt. | Kv$_{100}$, cSt | Kv$_{40}$, cSt | Viscosity Index | TGA Noack |
|---|---|---|---|---|---|
| Example 1 | 300.5 | 5.55 | 31.12 | 116 | 10.1 |
| Example 2 | 300.5 | 4.63 | 26.18 | 87 | 14.4 |

The fluids of Examples 1 and 2 are polar and have high VI. For example, AN5 (acrylonitrile) has VI of 76 versus these fluids have VI of 116 and 87. The performance of these fluids can be optimized by combination of olefin segment and thiol moiety. Besides 2-vinyl naphthalene used in Examples 1 and 2, one can use other aromatics such as 1-vinyl naphthalene. These fluids are like AN with built-in polar functionality that may improve solvency and thermal and oxidative stability.

These sulfur-containing fluids show improved viscosity/volatility characteristics.

All these fluids are stable Group V base stocks.

Example 4

Reaction of vinylidene double bond terminated 1-octene dimer (C$_{16}$=) and (3-mercaptopropyl)methyldimethoxysilane

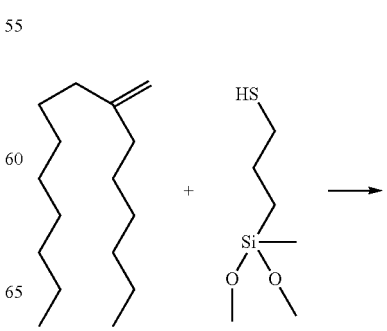

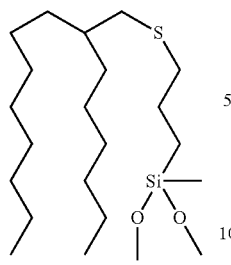

Vinylidene double bond terminated 1-octene dimer ($C_{16}=$) (5.0 grams, 22.28 mmol, MW: 224.43, 1.0 equivalent), (3-mercaptopropyl)methyldimethoxysilane (4.82 grams, 26.73 mmole, MW: 180.34, 1.2 equivalent) and 2,2'-azobis(2-methylpropionitrile) (AIBN) (0.365 grams, 2.23 mmol, MW: 164.0, 0.1 equivalent) were charged in a 25 milliliter thick sealed glass reactor. After addition, the reaction mixture was stirred for 20 hours at 110° C. The reaction was then stopped and cooled down to room temperature. The unreacted (3-mercaptopropyl)methyldimethoxysilane and high boiling component were distilled by air bath oven at 200° C. under vacuum for 1 hour. The $^1$H NMR showed the conversion of vinylidene double bond and the formation of thioether linkage (—$CH_2$—S—$CH_2$—). The structure of the final product was determined by $^1$HNMR and IR. Yield: 6.0 grams (65%). $^1$H NMR ($CDCl_3$): 3.40 (6H, s), 2.37 (4H, m), 1.53-1.40 (3H, m) 1.27 (29H, m), 0.77 (9H, t), 0.67 (2H, t). IR: ($cm^{-1}$): 2956, 2925, 2854, 2834, 1465, 1377, 1258, 1189, 1089, 834, 768, 724.

Example 5

Reaction of vinylidene double bond terminated 1-octene dimer ($C_{16}=$) and (3-mercaptopropyl)trimethoxysilane

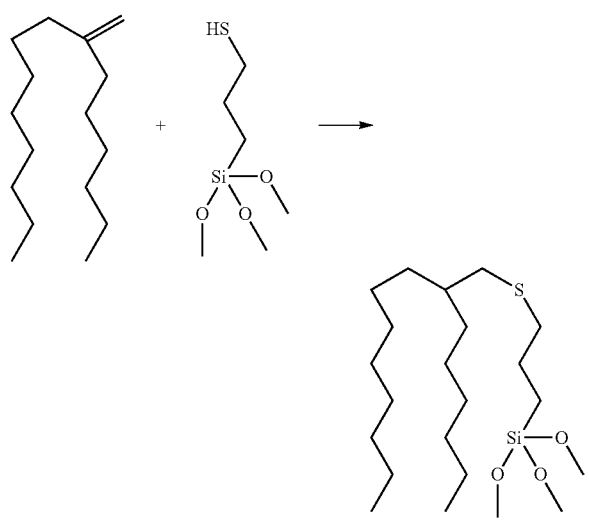

Vinylidene double bond terminated 1-octene dimer ($C_{16}=$) (5.0 grams, 22.28 mmol, MW: 224.43, 1.0 equivalent), (3-mercaptopropyl)trimethoxysilane (5.25 grams, 26.73 mmole, MW: 196.34, 1.2 equivalent) and 2,2'-azobis (2-methylpropionitrile) (AIBN) (0.365 grams, 2.23 mmol, MW: 164.0, 0.1 equivalent) were charged in a 25 milliliter thick sealed glass reactor. After addition, the reaction mixture was stirred for 60 hours at 120° C. The reaction was then stopped and cooled down to room temperature. The unreacted (3-mercaptopropyl)trimethoxysilane and high boiling component were distilled by air bath oven at 180° C. under vacuum for 1 hour. The $^1$H NMR showed the conversion of vinylidene double bond and the formation of thioether linkage (—$CH_2$—S—$CH_2$—). The final product was determined by $^1$H NMR. Yield: 5.0 grams (53%). $^1$H NMR ($CDCl_3$): 3.57 (9H, s), 2.49 (4H, m), 1.69-1.54 (3H, m) 1.27 (22H, m), 0.89 (6H, t), 0.75 (2H). IR: ($cm^{-1}$): 2925, 2854, 1458, 1378, 1340, 1302, 1247, 1191, 1090, 815.

Example 6

Reaction of vinylidene double bond terminated 1-octene dimer ($C_{16}=$) and (3-mercaptopropyl) triethoxysilane

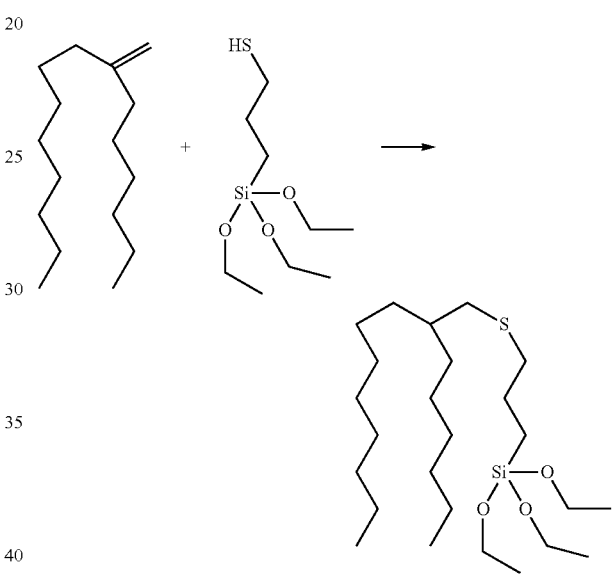

Vinylidene double bond terminated 1-octene dimer ($C_{16}=$) (5.0 grams, 22.28 mmol, MW: 224.43, 1.0 equivalent), (3-mercaptopropyl) triethoxysilane (6.37 grams, 26.73 mmol, MW: 238.42, 1.2 equivalent) and 2,2'-azobis(2-methylpropionitrile) (AIBN) (0.365 grams, 2.23 mmol, MW: 164.0, 0.1 equivalent) were charged in a 25 milliliter thick sealed glass reactor. After addition, the reaction mixture was stirred for 60 hours at 120° C. The reaction was then stopped and cooled down to room temperature. The unreacted (3-mercaptopropyl) triethoxysilane and high boiling component were distilled by air bath oven at 200° C. under vacuum for 1 hour. The $^1$H NMR showing the conversion of vinylidene double bond and the formation of thioether linkage (—$CH_2$—S—$CH_2$—). The final product was determined by $^1$HNMR. Yield: 7.0 grams (68%). $^1$H NMR ($CDCl_3$): 3.76 (6H, t), 2.41 (4H, m), 1.91-1.61 (3H, m) 1.27 (31H, m), 0.82 (8H, t), 0.67 (2H, t). IR: ($cm^{-1}$): 2925, 2854, 2733, 1457, 1389, 1340, 1295, 1248, 1166, 1103, 1080, 959, 785.

Example 7

Lube Properties of Base Stocks

The lube properties of the products of Examples 4-6 were evaluated and the data are shown below. The kinematic viscosity (Kv) of the liquid product was measured using ASTM standards D-445 and reported at temperatures of 100° C. (Kv at 100° C.) or 40° C. (Kv at 40° C.). The viscosity index (VI) was measured according to ASTM standard D-2270 using the measured kinematic viscosities for each product. The product volatility was measured using thremogravimetric analysis (TGA) based Noack. Noack volatility was determined by ASTM D-5800.

| Basestock # | $Kv_{100}°$ C. | $Kv_{40}°$ C. | VI | TGA Noack |
|---|---|---|---|---|
| Example 4 | 2.28 | 7.32 | 129 | 24.63 |
| Example 5 | 2.56 | 8.47 | 141 | 17.38 |
| Example 6 | 2.65 | 8.55 | 160 | 14.26 |
| PAO2 | 1.7 | 5 | — | 99.73 |
| PAO4 | 4.10 | 19.00 | 126 | 13.45 |

The products were found to have good lubricant properties. All these synthetic basestocks have excellent viscosity index. The relative volatility of the basestocks along with PAO2 and PAO4 were measured using TGA Noack test. The results are shown in table above. The TGA Noack data of the fluids of Example 4-6 show that they have relatively low volatility compared to hydrocarbon fluids like PAO2 and PAO4.

Example 8

Synthesis of (2-(naphthalene-1-yl)ethyl)(octyl)sulfane

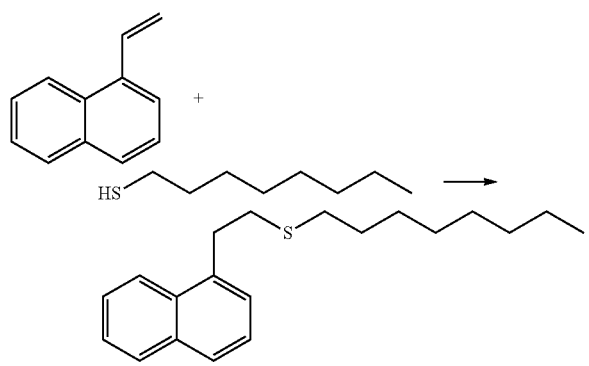

5.0 grams (32.4 mmol, MW: 154.21) 1-vinylnaphthalene, 7.1 grams (48.6 mmol, MW: 146.29) octanethiol and 0.266 grams (1.62 mmol, MW: 164.21) 2,2'-azobis(2-methylpropionitrile) (AIBN) were charged in a 25 milliliter thick sealed glass reactor. After addition, the reaction mixture was stirred for 68 hours at 110° C. The reaction was then stopped and cooled down to room temperature. The excess of unreacted octanethiol was removed by air bath oven at 200° C. under vacuum for 1 hour. The final product was determined by IR, $^1$HNMR. Yield: 8.8 grams (90%). IR: (cm$^{-1}$) 30045, 2924, 2853, 1596, 1510, 1459, 1394, 1377, 1261, 1219, 1165, 1016, 779, 730. $^1$H NMR (CDCl$_3$): 8.03-7.33 (7H, m), 3.32 (2H, t), 2.91 (2H, t), 2.55 (2H, t), 1.57 (2H, m) 1.46-1.27 (10H, m), 0.87 (3H, t).

Example 9

Synthesis of (2-ethylhexyl)(2-(naphthalene-1-yl)ethyl)sulfane

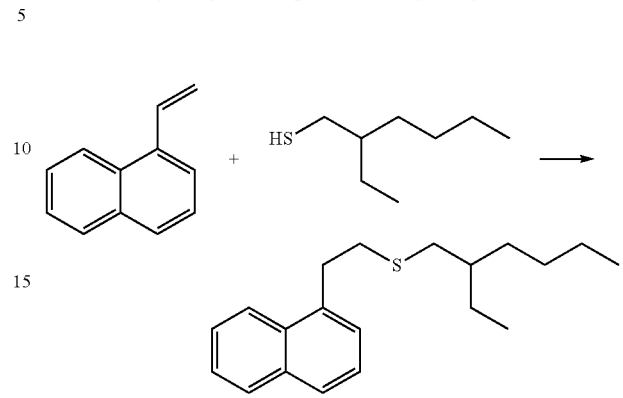

5.0 grams (32.4 mmol, MW: 154.21) 1-vinylnaphthalene, 7.1 grams (48.6 mmol, MW: 146.29) 2-ethylhexylthiol and 0.266 grams (1.62 mmol, MW: 164.21) 2,2'-azobis(2-methylpropionitrile) (AIBN) were charged in a 25 milliliter thick sealed glass reactor. After addition, the reaction mixture was stirred for 18 hours at 115° C. The reaction was then stopped and cooled down to room temperature. The excess of unreacted 2-ethylhexylthiol was removed by air bath oven at 200° C. under vacuum for 1 hour. The final product was determined by IR, $^1$HNMR. Yield: 8.1 grams (83%). IR: (cm$^{-1}$) 3046, 2957, 2926, 2870, 2857, 1596, 1510, 1458, 1394, 1378, 1260, 1265, 1077, 1016, 779, 730. $^1$H NMR (CDCl$_3$): 8.03-7.31 (7H, m), 3.35 (2H, t), 2.88 (2H, t), 2.54 (2H, t), (1.51-1.27 (10H, m), 0.87 (6H, m).

Example 10

Lube Properties of Base Stocks

The lube properties of the products of Examples 8 and 9 were evaluated and the data are shown below. The kinematic viscosity (Kv) of the liquid product was measured using ASTM standards D-445 and reported at temperatures of 100° C. (Kv at 100° C.) or 40° C. (Kv at 40° C.). The viscosity index (VI) was measured according to ASTM standard D-2270 using the measured kinematic viscosities for each product. The product volatility was measured using thremogravimetric analysis (TGA) based Noack. Noack volatility was determined by ASTM D-5800.

| Basestock # | MW | $Kv_{100}°$ C. | $Kv_{40}°$ C. | VI | TGA Noack |
|---|---|---|---|---|---|
| Example 8 | 300.5 | 3.95 | 21.88 | 52 | 9.9 |
| Example 9 | 300.5 | 3.71 | 23.17 | −189 | 13.36 |

The products were found to have good lubricant properties.

PCT and EP Clauses:

1. A composition comprising one or more sulfur-containing compounds represented by the formula $(R_1)_a(X)(R_2)_b$ wherein $R_1$ and $R_2$ are the same or different and are the residue of an olefin having from 4 to 40 carbon atoms, X is the residue of a thiol or polythiol, a is a value from 1 to 6, and b is a value from 0 to 6;

wherein the olefin is selected from the group consisting of an aliphatic olefin, an aromatic olefin, and a cycloaliphatic olefin; the thiol is selected from the group consisting of an aliphatic thiol, an aromatic thiol, a cycloaliphatic thiol, an ether-, ester- or acid-containing thiol, and a heteroatom-containing thiol, and the polythiol is selected from the group consisting of an aliphatic polythiol, an aromatic polythiol, a cycloaliphatic polythiol, an ether-, ester- or acid-containing polythiol, and a heteroatom-containing polythiol; and wherein the composition has a kinematic viscosity at a temperature of 100° C. ($Kv_{100}$), measured according to ASTM standard D-445, from 2 to 300 cst, a kinematic viscosity at a temperature of 40° C. ($Kv_{40}$), measured according to ASTM standard D-445, from 5 to 4000 cst, a viscosity index (VI), measured according to ASTM standard D-2270, from −100 to 300, and a Noack volatility, measured according to ASTM D-5800, of no greater than 90 percent.

2. The composition of clause 1 wherein
the aliphatic olefin is selected from polyalphaolefin dimer ($C_6$-$C_{40}$), trimer ($C_6$-$C_{40}$), tetramer ($C_6$-$C_{40}$), pentamer ($C_6$-$C_{40}$), and hexamer ($C_6$-$C_{40}$), and alpha-olefin ($C_4$-$C_{40}$);

the aromatic olefin is selected from 2,4-dimethylstyrene, 2,5-dimethylstyrene, 4-tert-butylstyrene, 4-tert-butoxystyrene, 3,4-dimethoxystyrene, 4-acetoxystyrene, 1,3-diisopropenylbenzene, 4-ethoxystyrene, 2,3,4,5,6-pentafluorostyrene, 4-fluorostyrene, 1-(trifluoromethyl)-4-vinylbenzene, 4-[N-(methylaminoethyl)aminomethyl]styrene, 4-benzyloxy-3-methoxystyrene, 2-methoxy-4-vinylphenol, ((4-vinylphenyl)methylene)dibenzene, 1-vinylnaphthalene, 2-vinylnaphthalene, divinylbenzene, trivinylbenzene, styrene, 4-methyl styrene, 2-methyl styrene, 1-methyl styrene, 4-methoxystyrene, 2-methoxystyrene, 1-allyl-4-(trifluoromethyl)benzene, 9-vinylanthracene, 1,1-diphenylethylene, 2,3-dibenzyl-1,3-butadiene, 1-allyl-2-methylbenzene, dipentene, 4-vinylbiphenyl, 9-vinylcarbazole, N-vinylphthalimide, and 4-(trifluoromethyl)styrene; and the cycloaliphatic olefin is selected from vinylcyclopentane, vinylcylcohexane, allylcyclohexane, 1,2,4-trivinylcyclohexane, and 5-vinyl-2-norbornene.

3. The composition of clauses 1 and 2 wherein:
the aliphatic thiol is selected from 1-butanethiol, 1-hexanethiol, 1-octanethiol, 1-decanethiol, 1-dodecanethiol, 1-hexadecanethiol, and 1-octadecanethiol;

the aromatic thiol is selected from thiophenol, 4-methylbenzenethiol, 4-methoxythiophenol, benzyl mercaptan, 4-mercaptopyridine, 2-mercaptopyrimidine, 1-naphthalenethiol, and 2-naphthalenethiol;

the cycloaliphatic thiol is selected from cyclohexanethiol, cyclopentanethiol, 2-methylcyclopentanethiol, cyclodecanethiol, cyclododecanethiol, 3-decylcyclopentanethiol, (mercaptomethyl)cyclohexane, 3-isopropylcycloheptanethiol, and 4-(2-mercaptoethyl)cyclohexanethiol;

the ether-, ester- or acid-containing thiol is selected from butyl 3-mercaptopropionic acid, isooctyl 3-mercaptopropionate, methyl 3-mercaptopropionate, 3-mercaptopropionic acid, 2-ethylhexyl 2-mercaptoacetate, ethyl 2-mercaptopropionic acid, and thioglycolic acid; and the heteroatom-containing thiol is selected from 3-mercaptopropyl)methyldimethoxysilane, 3-mercaptopropyl)trimethoxysilane, and 3-mercaptopropyl) triethoxysilane.

4. The composition of clauses 1 and 2 wherein:
the aliphatic polythiol is selected from 1,2-ethanedithiol, 1,3-propanedithiol, 1,4-butanedithiol, 1,5-pentanedithiol, 1,6-hexanedithiol, 1,8-octanedithiol, 1,9-nonanedithiol, 1,11-undecanedithiol, and 1,16-hexadecanedithiol;

the aromatic polythiol is selected from benzene-1,2-dithiol, benzene-1,3-dithiol, toluene-3,4-dithiol, 5-phenyl-1,3,4-oxadiazole-2-thiol, 1,3,4-thiodizole-2,5-dithiol, 1,2,4-thiadiazole-3,5-dithiol, 1,2-benzenedimethanedithiol, 1,3-benzenedimethanedithiol, and 1,4-benzenedimethanedithiol;

the cycloaliphatic polythiol is selected from 1,5-cyclooctanedithiol, 4-hexyl-1,2-cyclohexanedithiol, and p-menthane-2,9-dithiol;

the ether-, ester- or acid-containing polythiol is selected from 2-mercaptoethyl ether, 2,2'-(ethylenedioxy)diethanethiol, hexa(ethylene glycol)dithiol, trimethylolpropane tris(3-mercaptopropionate), pentaerythritol tetrakis(3-mercaptopropionate); and the heteroatom-containing polythiol is selected from, 2-thizoline-2-thiol, 2-mercaptobenzothiazole, 5-methoxylbenzoxazole-2-thiol, 5-phenyl-1H-1,2,4-trizole-3-thiol, 1H-1,24-trizole-3-thiol, 5-phenyl-1,3,4-oxadiazole-2-thiol, 2-thiazoline-2-thiol, 2-mercaptobenzothiazole, 5-methoxybenzoxazole-2-thiol, 4-phenylimidazole-2-thiol, 2-mercaptoimidazole, 1H-1,2,4-trizole-3-thiol, 5-phenyl-1,3,4-oxadiazole-2-thiol 1,3,4-thiodizole-2,5-dithiol, and 1,2,4-thiadiazole-3,5-dithiol.

5. The composition of clauses 1-4 which has a kinematic viscosity at a temperature of 100° C. ($Kv_{100}$), measured according to ASTM standard D-445, from 2.2 to 200 cst, a kinematic viscosity at a temperature of 40° C. ($Kv_{40}$), measured according to ASTM standard D-445, from 20 to 2000 cst, a viscosity index (VI), measured according to ASTM standard D-2270, from 50 to 250, and a Noack volatility, measured according to ASTM D-5800, of no greater than 50 percent.

6. A composition comprising one or more sulfur-containing compounds, wherein said one or more sulfur-containing compounds are produced by a process which comprises:
reacting an olefin with a thiol or polythiol, optionally in the presence of a catalyst, under thiol-ene reaction conditions sufficient to produce the one or more sulfur-containing compounds;

wherein the olefin is selected from the group consisting of an aliphatic olefin, an aromatic olefin, and a cycloaliphatic olefin; the thiol is selected from the group consisting of an aliphatic thiol, an aromatic thiol, a cycloaliphatic thiol, an ether-, ester- or acid-containing thiol, and a heteroatom-containing thiol; and the polythiol is selected from the group consisting of an aliphatic polythiol, aromatic polythiol, cycloaliphatic polythiol, an ether-, ester- or acid-containing polythiol, and a heteroatom-containing polythiol; and wherein the composition has a kinematic viscosity at a temperature of 100° C. ($Kv_{100}$), measured according to ASTM standard D-445, from 2 to 300 cst, a kinematic viscosity at a temperature of 40° C. ($Kv_{40}$), measured according to ASTM standard D-445, from 5 to 4000 cst, a viscosity index (VI), measured according to ASTM standard D-2270, from −100 to 300, and a Noack volatility, measured according to ASTM D-5800, of no greater than 90 percent.

7. A process for producing a composition comprising one or more sulfur-containing compounds, said process comprising:
reacting an olefin with a thiol or polythiol, optionally in the presence of a catalyst, under thiol-ene reaction conditions sufficient to produce said composition;

wherein the olefin is selected from the group consisting of an aliphatic olefin, an aromatic olefin, and a cycloaliphatic olefin; the thiol is selected from the group consisting of an aliphatic thiol, an aromatic thiol, a cycloaliphatic thiol, an ether-, ester- or acid-containing thiol, and a heteroatom-containing thiol; and the polythiol is selected from the group consisting of an aliphatic polythiol, aromatic polythiol, cycloaliphatic polythiol, an ether-, ester- or acid-containing polythiol, and a heteroatom-containing polythiol; and wherein the composition has a kinematic viscosity at a temperature of 100° C. ($Kv_{100}$), measured according to ASTM standard D-445, from 2 to 300 cst, a kinematic viscosity at a temperature of 40° C. ($Kv_{40}$), measured according to ASTM standard D-445, from 5 to 4000 cst, a viscosity index (VI), measured according to ASTM standard D-2270, from −100 to 300, and a Noack volatility, measured according to ASTM D-5800, of no greater than 90 percent.

8. The process of clause 7 wherein
the aliphatic olefin is selected from polyalphaolefin dimer ($C_6$-$C_{40}$), trimer ($C_6$-$C_{40}$), tetramer ($C_6$-$C_{40}$), pentamer ($C_6$-$C_{40}$), and hexamer ($C_6$-$C_{40}$), and alpha-olefin ($C_4$-$C_{40}$);

the aromatic olefin is selected from 2,4-dimethylstyrene, 2,5-dimethylstyrene, 4-tert-butylstyrene, 4-tert-butoxystyrene, 3,4-dimethoxystyrene, 4-acetoxystyrene, 1,3-diisopropenylbenzene, 4-ethoxystyrene, 2,3,4,5,6-pentafluorostyrene, 4-fluorostyrene, 1-(trifluoromethyl)-4-vinylbenzene, 4-[N-(methylaminoethyl)aminomethyl]styrene, 4-benzyloxy-3-methoxystyrene, 2-methoxy-4-vinylphenol, ((4-vinylphenyl)methylene)dibenzene, 1-vinylnaphthalene, 2-vinylnaphthalene, divinylbenzene, trivinylbenzene, styrene, 4-methyl styrene, 2-methyl styrene, 1-methyl styrene, 4-methoxystyrene, 2-methoxystyrene, 1-allyl-4-(trifluoromethyl)benzene, 9-vinylanthracene, 1,1-diphenylethylene, 2,3-dibenzyl-1,3-butadiene, 1-allyl-2-methylbenzene, dipentene, 4-vinylbiphenyl, 9-vinylcarbazole, N-vinylphthalimide, and 4-(trifluoromethyl)styrene; and the cycloaliphatic olefin is selected from vinylcyclopentane, vinylcylcohexane, allylcyclohexane, 1,2,4-trivinylcyclohexane, and 5-vinyl-2-norbornene.

9. The process of clauses 7 and 8 wherein:
the aliphatic thiol is selected from 1-butanethiol, 1-hexanethiol, 1-octanethiol, 1-decanethiol, 1-dodecanethiol, 1-hexadecanethiol, and 1-octadecanethiol;

the aromatic thiol is selected from thiophenol, 4-methylbenzenethiol, 4-methoxythiophenol, benzyl mercapton, 4-mercaptopyridine, 2-mercaptopyrimidine, 1-naphthalenethiol, and 2-naphthalenethiol;

the cycloaliphatic thiol is selected from cyclohexanethiol, cyclopentanethiol, 2-methylcyclopentanethiol, cyclodecanethiol, cyclododecanethiol, 3-decylcyclopentanethiol, (mercaptomethyl)cyclohexane, 3-isopropylcycloheptanethiol, and 4-(2-mercaptoethyl)cyclohexanethiol;

the ether-, ester- or acid-containing thiol is selected from butyl 3-mercaptopropionic acid, isooctyl 3-mercaptopropionate, methyl 3-mercaptopropionate, 3-mercaptopropionic acid, 2-ethylhexyl 2-mercaptoacetate, ethyl 2-mercaptopropionic acid, and thioglycolic acid; and the heteroatom-containing thiol is selected from 3-mercaptopropyl)methyldimethoxysilane, 3-mercaptopropyl) trimethoxysilane, and 3-mercaptopropyl) triethoxysilane.

10. The process of clauses 7 and 8 wherein:
the aliphatic polythiol is selected from 1,2-ethanedithiol, 1,3-propanedithiol, 1,4-butanedithiol, 1,5-pentanedithiol, 1,6-hexanedithiol, 1,8-octanedithiol, 1,9-nonanedithiol, 1,11-undecanedithiol, and 1,16-hexadecanedithiol;

the aromatic polythiol is selected from benzene-1,2-dithiol, benzene-1,3-dithiol, toluene-3,4-dithiol, 5-phenyl-1,3,4-oxadiazole-2-thiol, 1,3,4-thiodizole-2,5-dithiol, 1,2,4-thiadiazole-3,5-dithiol, 1,2-benzenedimethanedithiol, 1,3-benzenedimethanedithiol, and 1,4-benzenedimethanedithiol;

the cycloaliphatic polythiol is selected from 1,5-cyclooctanedithiol, 4-hexyl-1,2-cyclohexanedithiol, and p-menthane-2,9-dithiol;

the ether-, ester- or acid-containing polythiol is selected from 2-mercaptoethyl ether, 2,2'-(ethylenedioxy)diethanethiol, hexa(ethylene glycol)dithiol, trimethylolpropane tris(3-mercaptopropionate), pentaerythritol tetrakis(3-mercaptopropionate); and the heteroatom-containing polythiol is selected from, 2-thizoline-2-thiol, 2-mercaptobenzothiazole, 5-methoxylbenzoxazole-2-thiol, 5-phenyl-1H-1,2,4-trizole-3-thiol, 1H-1,24-trizole-3-thiol, 5-phenyl-1,3,4-oxadiazole-2-thiol, 2-thiazoline-2-thiol, 2-mercaptobenzothiazole, 5-methoxybenzoxazole-2-thiol, 4-phenylimidazole-2-thiol, 2-mercaptoimidazole, 1H-1,2,4-trizole-3-thiol, 5-phenyl-1,3,4-oxadiazole-2-thiol 1,3,4-thiodizole-2,5-dithiol, and 1,2,4-thiadiazole-3,5-dithiol.

11. A lubricating oil base stock comprising one or more compounds represented by the formula

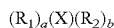

$(R_1)_a(X)(R_2)_b$ wherein $R_1$ and $R_2$ are the same or different and are the residue of an olefin having from 4 to 40 carbon atoms, X is the residue of a thiol or polythiol, $\underline{a}$ is a value from 1 to 6, and $\underline{b}$ is a value from 0 to 6;

wherein the olefin is selected from the group consisting of an aliphatic olefin, an aromatic olefin, and a cycloaliphatic olefin; the thiol is selected from the group consisting of an aliphatic thiol, an aromatic thiol, a cycloaliphatic thiol, an ether-, ester- or acid-containing thiol, and a heteroatom-containing thiol; and the polythiol is selected from the group consisting of an aliphatic polythiol, aromatic polythiol, cycloaliphatic polythiol, an ether-, ester- or acid-containing polythiol, and a heteroatom-containing polythiol; and wherein the lubricating oil base stock has a kinematic viscosity at a temperature of 100° C. ($Kv_{100}$), measured according to ASTM standard D-445, from 2 to 300 cst, a kinematic viscosity at a temperature of 40° C. ($Kv_{40}$), measured according to ASTM standard D-445, from 5 to 4000 cst, a viscosity index (VI), measured according to ASTM standard D-2270, from −100 to 300, and a Noack volatility, measured according to ASTM D-5800, of no greater than 90 percent.

12. A lubricating oil comprising a lubricating oil base stock as a major component, and a sulfur-containing cobase stock as a minor component; wherein said sulfur-containing cobase stock comprises one or more compounds represented by the formula

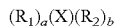

$(R_1)_a(X)(R_2)_b$ wherein $R_1$ and $R_2$ are the same or different and are the residue of an olefin having from 4 to 40 carbon atoms, X is the residue of a thiol or polythiol, $\underline{a}$ is a value from 1 to 6, and $\underline{b}$ is a value from 0 to 6;

wherein the olefin is selected from the group consisting of an aliphatic olefin, an aromatic olefin, and a cycloaliphatic olefin; the thiol is selected from the group consisting of an aliphatic thiol, an aromatic thiol, a cycloaliphatic thiol, an ether-, ester- or acid-containing thiol, and a heteroatom-containing thiol; and the polythiol is selected from the group consisting of an aliphatic polythiol, aromatic polythiol, cycloaliphatic polythiol, an ether-, ester- or acid-containing polythiol, and a heteroatom-containing polythiol; and wherein the sulfur-containing cobase stock has a kinematic viscosity at a temperature of 100° C. ($Kv_{100}$), measured according to ASTM standard D-445, from 2 to 300 cst, a kinematic viscosity at a temperature of 40° C. ($Kv_{40}$), measured according to ASTM standard D-445, from 5 to 4000 cst, a viscosity index (VI), measured according to ASTM standard D-2270, from −100 to 300, and a Noack volatility, measured according to ASTM D-5800, of no greater than 90 percent.

13. The lubricating oil of clause 12 wherein the lubricating oil base stock is present in an amount from 50 weight percent to 99 weight percent, and the sulfur-containing hydrocarbon cobase stock is present in an amount from 1 weight percent to 50 weight percent, based on the total weight of the lubricating oil.

14. The lubricating oil of clauses 12 and 13 further comprising one or more of a viscosity improver, antioxidant, detergent, dispersant, pour point depressant, corrosion inhibitor, metal deactivator, seal compatibility additive, antifoam agent, inhibitor, and anti-rust additive.

15. A method for improving one or more of solubility and dispersancy of polar additives in a lubricating oil by using as the lubricating oil a formulated oil comprising a lubricating oil base stock as a major component, and a sulfur-containing cobase stock as a minor component; wherein said sulfur-containing cobase stock comprises one or more compounds represented by the formula $(R_1)_a(X)(R_2)_b$ wherein $R_1$ and $R_2$ are the same or different and are the residue of an olefin having from 4 to 40 carbon atoms, X is the residue of a thiol or polythiol, $\underline{a}$ is a value from 1 to 6, and $\underline{b}$ is a value from 0 to 6;

wherein the olefin is selected from the group consisting of an aliphatic olefin, an aromatic olefin, and a cycloaliphatic olefin; the thiol is selected from the group consisting of an aliphatic thiol, an aromatic thiol, a cycloaliphatic thiol, an ether-, ester- or acid-containing thiol, and a heteroatom-containing thiol; and the polythiol is selected from the group consisting of an aliphatic polythiol, aromatic polythiol, cycloaliphatic polythiol, an ether-, ester- or acid-containing polythiol, and a heteroatom-containing polythiol; and wherein the sulfur-containing cobase stock has a kinematic viscosity at a temperature of 100° C. ($Kv_{100}$), measured according to ASTM standard D-445, from 2 to 300 cst, a kinematic viscosity at a temperature of 40° C. ($Kv_{40}$), measured according to ASTM standard D-445, from 5 to 4000 cst, a viscosity index (VI), measured according to ASTM standard D-2270, from −100 to 300, and a Noack volatility, measured according to ASTM D-5800, of no greater than 90 percent.

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A composition comprising one or more sulfur-containing compounds represented by the formula $(R_1)_a(X)(R_2)_b$ wherein $R_1$ and $R_2$ are the same or different and are the residue of an olefin having from 4 to 40 carbon atoms, X is the residue of a polythiol, $\underline{a}$ is a value from 1 to 6, and $\underline{b}$ is a value from 0 to 6;

wherein the olefin is selected from the group consisting of an aliphatic olefin, an aromatic olefin, and a cycloaliphatic olefin; and the polythiol is selected from the group consisting of an aliphatic polythiol, an aromatic polythiol, a cycloaliphatic polythiol, an ether-, ester- or acid-containing polythiol, and a heteroatom-containing polythiol; and wherein the composition has a kinematic viscosity at a temperature of 100° C. ($Kv_{100}$), measured according to ASTM standard D-445, from 2 to 300 cst, a kinematic viscosity at a temperature of 40° C. ($Kv_{40}$), measured according to ASTM standard D-445, from 5 to 4000 cst, a viscosity index (VI), measured according to ASTM standard D-2270, from −100 to 300, and a Noack volatility, measured according to ASTM D-5800, of no greater than 90 percent.

2. The composition of claim 1 wherein:
the aliphatic olefin is selected from polyalphaolefin dimer ($C_6$-$C_{40}$), trimer ($C_6$-$C_{40}$), tetramer ($C_6$-$C_{40}$), pentamer ($C_6$-$C_{40}$), and hexamer ($C_6$-$C_{40}$), and alpha-olefin ($C_4$-$C_{40}$).

3. The composition of claim 1 wherein:
the aromatic olefin is selected from 2,4-dimethylstyrene, 2,5-dimethylstyrene, 4-tert-butylstyrene, 4-tert-butoxystyrene, 3,4-dimethoxystyrene, 4-acetoxystyrene, 1,3-diisopropenylbenzene, 4-ethoxystyrene, 2,3,4,5,6-pentafluorostyrene, 4-fluorostyrene, 1-(trifluoromethyl)-4-vinylbenzene, 4-[N-(methylaminoethyl)aminomethyl] styrene, 4-benzyloxy-3-methoxystyrene, 2-methoxy-4-vinylphenol, ((4-vinylphenyl)methylene)dibenzene, 1-vinylnaphthalene, 2-vinylnaphthalene, divinylbenzene, trivinylbenzene, styrene, 4-methyl styrene, 2-methyl styrene, 1-methyl styrene, 4-methoxystyrene, 2-methoxystyrene, 1-allyl-4-(trifluoromethyl)benzene, 9-vinylanthracene, 1,1-diphenylethylene, 2,3-dibenzyl-1,3-butadiene, 1-allyl-2-methylbenzene, dipentene, 4-vinylbiphenyl, 9-vinylcarbazole, N-vinylphthalimide, and 4-(trifluoromethyl)styrene.

4. The composition of claim 1 wherein:
the cycloaliphatic olefin is selected from vinylcyclopentane, vinylcyclohexane, allylcyclohexane, 1,2,4-trivinylcyclohexane, and 5-vinyl-2-norbornene.

5. The composition of claim 1 wherein:
the aliphatic polythiol is selected from 1,2-ethanedithiol, 1,3-propanedithiol, 1,4-butanedithiol, 1,5-pentanedithiol, 1,6-hexanedithiol, 1,8-octanedithiol, 1,9-nonanedithiol, 1,11-undecanedithiol, and 1,16-hexadecanedithiol;
the aromatic polythiol is selected from benzene-1,2-dithiol, benzene-1,3-dithiol, toluene-3,4-dithiol, 5-phenyl-1,3,4-oxadiazole-2-thiol, 1,3,4-thiodizole-2,5-dithiol, 1,2,4-thiadiazole-3,5-dithiol, 1,2- benzenedimethanedithiol, 1,3-benzenedimethanedithiol, and 1,4-benzenedimethanedithiol;

the cycloaliphatic polythiol is selected from 1,5-cyclooctanedithiol, 4-hexyl-1,2-cyclohexanedithiol, and p-menthane-2,9-dithiol;

the ether-, ester- or acid-containing polythiol is selected from 2-mercaptoethyl ether, 2,2'-(ethylenedioxy)diethanethiol, hexa(ethylene glycol)dithiol, trimethylolpropane tris(3-mercaptopropionate), pentaerythritol tetrakis(3-mercaptopropionate); and the heteroatom-containing polythiol is selected from, 2-thizoline-2-thiol, 2-mercaptobenzothiazole, 5-methoxylbenzoxazole-2-thiol, 5-phenyl-1H-1,2,4-trizole-3-thiol, 1H-1,24-trizole-3-thiol, 5-phenyl-1,3,4-oxadiazole-2-thiol, 2-thiazoline-2-thiol, 2-mercaptobenzothiazole, 5-methoxybenzoxazole-2-thiol, 4-phenylimidazole-2-thiol, 2-mercaptoimidazole, 1H-1,2,4-trizole-3-thiol, 5-phenyl-1,3,4-oxadiazole-2-thiol 1,3,4-thiodizole-2,5-dithiol, and 1,2,4-thiadiazole-3,5-dithiol.

6. The composition of claim 1 which has a kinematic viscosity at a temperature of 100° C. ($Kv_{100}$), measured according to ASTM standard D-445, from 2.2 to 200 cst, a kinematic viscosity at a temperature of 40° C. ($Kv_{40}$), measured according to ASTM standard D-445, from 20 to 2000 cst, a viscosity index (VI), measured according to ASTM standard D-2270, from 50 to 250, and a Noack volatility, measured according to ASTM D-5800, of no greater than 50 percent.

7. A composition comprising one or more sulfur-containing compounds, wherein said one or more sulfur-containing compounds are produced by a process which comprises:

reacting an olefin with a polythiol, optionally in the presence of a catalyst, under thiol-ene reaction conditions sufficient to produce the one or more sulfur-containing compounds;

wherein the olefin is selected from the group consisting of an aliphatic olefin, an aromatic olefin, and a cycloaliphatic olefin; and the polythiol is selected from the group consisting of an aliphatic polythiol, aromatic polythiol, cycloaliphatic polythiol, an ether-, ester- or acid-containing polythiol, and a heteroatom-containing polythiol; and wherein the composition has a kinematic viscosity at a temperature of 100° C. ($Kv_{100}$), measured according to ASTM standard D-445, from 2 to 300 cst, a kinematic viscosity at a temperature of 40° C. ($Kv_{40}$), measured according to ASTM standard D-445, from 5 to 4000 cst, a viscosity index (VI), measured according to ASTM standard D-2270, from −100 to 300, and a Noack volatility, measured according to ASTM D-5800, of no greater than 90 percent.

8. A process for producing a composition comprising one or more sulfur-containing compounds, said process comprising:

reacting an olefin with a polythiol, optionally in the presence of a catalyst, under thiol-ene reaction conditions sufficient to produce said composition;

wherein the olefin is selected from the group consisting of an aliphatic olefin, an aromatic olefin, and a cycloaliphatic olefin; and the polythiol is selected from the group consisting of an aliphatic polythiol, aromatic polythiol, cycloaliphatic polythiol, an ether-, ester- or acid-containing polythiol, and a heteroatom-containing polythiol; and wherein the composition has a kinematic viscosity at a temperature of 100° C. ($Kv_{100}$), measured according to ASTM standard D-445, from 2 to 300 cst, a kinematic viscosity at a temperature of 40° C. ($Kv_{40}$), measured according to ASTM standard D-445, from 5 to 4000 cst, a viscosity index (VI), measured according to ASTM standard D-2270, from −100 to 300, and a Noack volatility, measured according to ASTM D-5800, of no greater than 90 percent.

9. The process of claim 8 wherein:

the aliphatic olefin is selected from polyalphaolefin dimer ($C_6$-$C_{40}$), trimer ($C_6$-$C_{40}$), tetramer ($C_6$-$C_{40}$), pentamer ($C_6$-$C_{40}$), and hexamer ($C_6$-$C_{40}$), and alpha-olefin ($C_4$-$C_{40}$).

10. The process of claim 8 wherein:

the aromatic olefin is selected from 2,4-dimethylstyrene, 2,5-dimethylstyrene, 4-tert-butylstyrene, 4-tert-butoxystyrene, 3,4-dimethoxystyrene, 4-acetoxystyrene, 1,3-diisopropenylbenzene, 4-ethoxystyrene, 2,3,4,5,6-pentafluorostyrene, 4-fluorostyrene, 1-(trifluoromethyl)-4-vinylbenzene, 4-[N-(methylaminoethyl)aminomethyl] styrene, 4-benzyloxy-3-methoxystyrene, 2-methoxy-4-vinylphenol, ((4-vinylphenyl)methylene)dibenzene, 1-vinylnaphthalene, 2-vinylnaphthalene, divinylbenzene, trivinylbenzene, styrene, 4-methyl styrene, 2-methyl styrene, 1-methyl styrene, 4-methoxystyrene, 2-methoxystyrene, 1-allyl-4-(trifluoromethyl)benzene, 9-vinylanthracene, 1,1-diphenylethylene, 2,3-dibenzyl-1,3-butadiene, 1-allyl-2-methylbenzene, dipentene, 4-vinylbiphenyl, 9-vinylcarbazole, N-vinylphthalimide, and 4-(trifluoromethyl)styrene.

11. The process of claim 8 wherein:

the cycloaliphatic olefin is selected from vinylcyclopentane, vinylcyclohexane, allylcyclohexane, 1,2,4-trivinylcyclohexane, and 5-vinyl-2-norbornene.

12. The process of claim 8 wherein:

the aliphatic polythiol is selected from 1,2-ethanedithiol, 1,3-propanedithiol, 1,4-butanedithiol, 1,5-pentanedithiol, 1,6-hexanedithiol, 1,8-octanedithiol, 1,9-nonanedithiol, 1,11-undecanedithiol, and 1,16-hexadecanedithiol;

the aromatic polythiol is selected from benzene-1,2-dithiol, benzene-1,3-dithiol, toluene-3,4-dithiol, 5-phenyl-1,3,4-oxadiazole-2-thiol, 1,3,4-thiodizole-2,5-dithiol, 1,2,4-thiadiazole-3,5-dithiol, 1,2-benzenedimethanedithiol, 1,3-benzenedimethanedithiol, and 1,4-benzenedimethanedithiol;

the cycloaliphatic polythiol is selected from 1,5-cyclooctanedithiol, 4-hexyl-1,2-cyclohexanedithiol, and p-menthane-2,9-dithiol;

the ether-, ester- or acid-containing polythiol is selected from 2-mercaptoethyl ether, 2,2'-(ethylenedioxy)diethanethiol, hexa(ethylene glycol)dithiol, trimethylolpropane tris(3-mercaptopropionate), pentaerythritol tetrakis(3-mercaptopropionate); and the heteroatom-containing polythiol is selected from, 2-thizoline-2-thiol, 2-mercaptobenzothiazole, 5-methoxylbenzoxazole-2-thiol, 5-phenyl-1H-1,2,4-trizole-3-thiol, 1H-1,24-trizole-3-thiol, 5-phenyl-1,3,4-oxadiazole-2-thiol, 2-thiazoline-2-thiol, 2-mercaptobenzothiazole, 5-methoxybenzoxazole-2-thiol, 4-phenylimidazole-2-thiol, 2-mercaptoimidazole, 1H-1,2,4-trizole-3-thiol, 5-phenyl-1,3,4-oxadiazole-2-thiol 1,3,4-thiodizole-2,5-dithiol, 1,2,4-thiadiazole-3,5-dithiol, 5-phenyl-1,3,4-oxadiazole-2-thiol, 1,3,4-thiodizole-2,5-dithiol, and 1,2,4-thiadiazole-3,5-dithiol.

13. A lubricating oil base stock comprising one or more compounds represented by the formula $(R_1)_a(X)(R_2)_b$ wherein $R_1$ and $R_2$ are the same or different and are the residue of an olefin having from 4 to 40 carbon atoms, X is the residue of a polythiol, a is a value from 1 to 6, and b is a value from 0 to 6;

wherein the olefin is selected from the group consisting of an aliphatic olefin, an aromatic olefin, and a cycloaliphatic olefin; and the polythiol is selected from the group consisting of an aliphatic polythiol, aromatic polythiol, cycloaliphatic polythiol, an ether-, ester- or acid-containing polythiol, and a heteroatom-containing polythiol; and wherein the lubricating oil base stock has a kinematic viscosity at a temperature of 100° C. ($Kv_{100}$), measured according to ASTM standard D-445, from 2 to 300 cst, a kinematic viscosity at a temperature of 40° C. ($Kv_{40}$), measured according to ASTM standard D-445, from 5 to 4000 cst, a viscosity index (VI), measured according to ASTM standard D-2270, from −100 to 300, and a Noack volatility, measured according to ASTM D-5800, of no greater than 90 percent.

14. The lubricating oil base stock of claim 13 which has a kinematic viscosity at a temperature of 100° C. ($Kv_{100}$), measured according to ASTM standard D-445, from 2.2 to 200 cst, a kinematic viscosity at a temperature of 40° C. ($Kv_{40}$), measured according to ASTM standard D-445, from 20 to 2000 cst, a viscosity index (VI), measured according to ASTM standard D-2270, from 50 to 250, and a Noack volatility, measured according to ASTM D-5800, of no greater than 50 percent.

15. A lubricating oil comprising a lubricating oil base stock as a major component, and a sulfur-containing cobase stock as a minor component; wherein said sulfur-containing cobase stock comprises one or more compounds represented by the formula $(R_1)_a(X)(R_2)_b$ wherein $R_1$ and $R_2$ are the same or different and are the residue of an olefin having from 4 to 40 carbon atoms, X is the residue of a polythiol, a is a value from 1 to 6, and b is a value from 0 to 6, wherein the olefin is selected from the group consisting of an aliphatic olefin, an aromatic olefin, and a cycloaliphatic olefin; and the polythiol is selected from the group consisting of an aliphatic polythiol, aromatic polythiol, cycloaliphatic polythiol, an ether-, ester- or acid-containing polythiol, and a heteroatom-containing polythiol; and wherein the sulfur-containing cobase stock has a kinematic viscosity at a temperature of 100° C. ($Kv_{100}$), measured according to ASTM standard D-445, from 2 to 300 cst, a kinematic viscosity at a temperature of 40° C. ($Kv_{40}$), measured according to ASTM standard D-445, from 5 to 4000 cst, a viscosity index (VI), measured according to ASTM standard D-2270, from −100 to 300, and a Noack volatility, measured according to ASTM D-5800, of no greater than 90 percent.

16. The lubricating oil of claim 15 wherein the lubricating oil base stock comprises a Group V base oil stock.

17. The lubricating oil of claim 15 wherein the sulfur-containing cobase stock has a kinematic viscosity at a temperature of 100° C. ($Kv_{100}$), measured according to ASTM standard D-445, from 2.2 to 200 cst, a kinematic viscosity at a temperature of 40° C. ($Kv_{40}$), measured according to ASTM standard D-445, from 20 to 2000 cst, a viscosity index (VI), measured according to ASTM standard D-2270, from 50 to 250, and a Noack volatility, measured according to ASTM D-5800, of no greater than 50 percent.

18. The lubricating oil of claim 15 wherein the lubricating oil base stock is present in an amount from 50 weight percent to 99 weight percent, and the sulfur-containing hydrocarbon cobase stock is present in an amount from 1 weight percent to 50 weight percent, based on the total weight of the lubricating oil.

19. The lubricating oil of claim 15 further comprising one or more of a viscosity improver, antioxidant, detergent, dispersant, pour point depressant, corrosion inhibitor, metal deactivator, seal compatibility additive, anti-foam agent, inhibitor, and anti-rust additive.

20. A method for improving one or more of solubility and dispersancy of polar additives in a lubricating oil by using as the lubricating oil a formulated oil comprising a lubricating oil base stock as a major component, and a sulfur-containing cobase stock as a minor component; wherein said sulfur-containing cobase stock comprises one or more compounds represented by the formula $(R_1)_a(X)(R_2)_b$ wherein $R_1$ and $R_2$ are the same or different and are the residue of an olefin having from 4 to 40 carbon atoms, X is the residue of a polythiol, a is a value from 1 to 6, and b is a value from 0 to 6;

wherein the olefin is selected from the group consisting of an aliphatic olefin, an aromatic olefin, and a cycloaliphatic olefin; and the polythiol is selected from the group consisting of an aliphatic polythiol, aromatic polythiol, cycloaliphatic polythiol, an ether-, ester- or acid-containing polythiol, and a heteroatom-containing polythiol; and wherein the sulfur-containing cobase stock has a kinematic viscosity at a temperature of 100° C. ($Kv_{100}$), measured according to ASTM standard D-445, from 2 to 300 cst, a kinematic viscosity at a temperature of 40° C. ($Kv_{40}$), measured according to ASTM standard D-445, from 5 to 4000 cst, a viscosity index (VI), measured according to ASTM standard D-2270, from −100 to 300, and a Noack volatility, measured according to ASTM D-5800, of no greater than 90 percent.

21. The method of claim 20 wherein the sulfur-containing cobase stock has a kinematic viscosity at a temperature of 100° C. ($Kv_{100}$), measured according to ASTM standard D-445, from 2.2 to 200 cst, a kinematic viscosity at a temperature of 40° C. ($Kv_{40}$), measured according to ASTM standard D-445, from 20 to 2000 cst, a viscosity index (VI), measured according to ASTM standard D-2270, from 50 to 250, and a Noack volatility, measured according to ASTM D-5800, of no greater than 50 percent.

22. The method of claim 20 wherein the formulated oil further comprises one or more of a viscosity improver, antioxidant, detergent, dispersant, pour point depressant, corrosion inhibitor, metal deactivator, seal compatibility additive, anti-foam agent, inhibitor, and anti-rust additive.

* * * * *